United States Patent
Costentin et al.

(10) Patent No.: US 10,125,427 B2
(45) Date of Patent: Nov. 13, 2018

(54) PORPHYRIN MOLECULAR CATALYSTS FOR SELECTIVE ELECTROCHEMICAL REDUCTION OF $CO_2$ INTO CO

(71) Applicants: CENTRE NATIONAL DE LA RECHERCHE SCIENTIFIQUE (CNRS), Paris (FR); UNIVERSITE PARIS DIDEROT PARIS 7, Paris (FR)

(72) Inventors: Cyrille Costentin, Montreuil (FR); Marc Robert, Paris (FR); Samuel Drouet, Cerences (FR); Guillaume Passard, Saint Denis de Gastines (FR); Jean-Michel Saveant, Paris (FR); Arnaud Tatin, Paris (FR)

(73) Assignees: CENTRE NATIONAL DE LA RECHERCHE SCIENTIFIQUE (CNRS), Paris (FR); UNIVERSITE PARIS DIDEROT PARIS 7, Paris (FR)

( * ) Notice: Subject to any disclaimer, the term of this patent is extended or adjusted under 35 U.S.C. 154(b) by 219 days.

(21) Appl. No.: 15/309,035

(22) PCT Filed: May 4, 2015

(86) PCT No.: PCT/EP2015/059746
§ 371 (c)(1),
(2) Date: Nov. 4, 2016

(87) PCT Pub. No.: WO2015/169763
PCT Pub. Date: Nov. 12, 2015

(65) Prior Publication Data
US 2017/0067168 A1   Mar. 9, 2017

(30) Foreign Application Priority Data

May 5, 2014 (EP) .................................. 14305660
Feb. 2, 2015 (EP) .................................. 15020013

(51) Int. Cl.
  C25B 1/00 (2006.01)
  C01B 32/40 (2017.01)
  (Continued)

(52) U.S. Cl.
  CPC ............... *C25B 1/00* (2013.01); *C01B 32/40* (2017.08); *C07D 487/22* (2013.01);
  (Continued)

(58) Field of Classification Search
  CPC ... C25D 1/00; C01B 32/40; C25B 11/12; C25B 9/00; C07F 15/025; C07F 487/22
  See application file for complete search history.

(56) References Cited

U.S. PATENT DOCUMENTS 3,687,863 A * 8/1972 Wacher ............... G02B 5/223
                                                        252/582
4,892,941 A * 1/1990 Dolphin ............... B01J 31/1815
                                                        530/505

(Continued)

OTHER PUBLICATIONS

Weng, et al. Journal of the American Chemical Society 2016 138 (26), 8076-8079DOI: 10.1021/jacs.6b04746 (Year: 2016).*

(Continued)

*Primary Examiner* — Louis J Rufo
(74) *Attorney, Agent, or Firm* — Birch, Stewart, Kolasch & Birch, LLP

(57) ABSTRACT

The present invention relates to porphyrins of formula (I): wherein $R^1$ to $R^6$, $R^{1'}$ to $R^{6'}$, X, X' Y and Y' are as described in claim 1. The invention also relates to complexes of said porphyrins with transition metals, in particular iron, preferably as Fe(III) or Fe(0) complex, and salts thereof, use thereof as catalysts for the selective electrochemical reduction of $CO_2$ into CO, electrochemical cells comprising said complexes, and a method for selectively reducing electrochemically $CO_2$ into CO using said complexes.

(Continued)

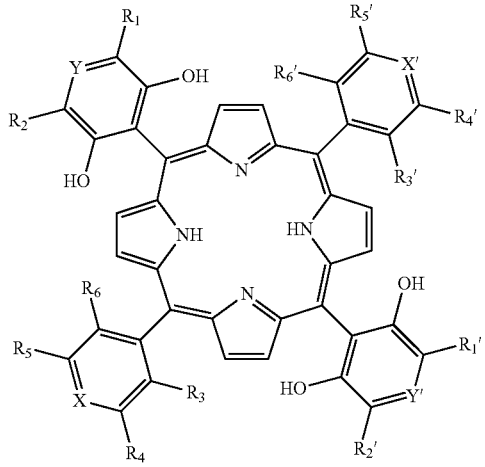

(I)

19 Claims, 4 Drawing Sheets

(51) Int. Cl.
  *C25B 11/12* (2006.01)
  *C25B 9/00* (2006.01)
  *C07F 15/02* (2006.01)
  *C07D 487/22* (2006.01)

(52) U.S. Cl.
  CPC .............. *C07F 15/025* (2013.01); *C25B 9/00* (2013.01); *C25B 11/12* (2013.01)

(56) References Cited

U.S. PATENT DOCUMENTS

| | | | | |
|---|---|---|---|---|
| 5,204,215 A * | 4/1993 | Kishii | ................. | C07D 487/22 365/119 |
| 6,103,714 A * | 8/2000 | Fridovich | ............ | A61K 31/409 514/185 |
| 2006/0030718 A1* | 2/2006 | Zhang | ................. | C07D 487/22 548/954 |
| 2015/0096899 A1* | 4/2015 | Costentin | ................. | C25B 9/06 205/555 |

OTHER PUBLICATIONS

Puttaiah, B. & Karunanithi, K. J Chem Sci (2016) 128: 501. https://doi.org/10.1007/s12039-016-1053-9 (Year: 2016).*
Bhugun et al., "Catalysis of the Electrochemical Reduction of Carbon Dioxide by Iron(0) Porphyrins. Synergistic Effect of Lewis Acid Cations," J. Phys. Chem., vol. 100, No. 51, 1996 (Abstract published Nov. 15, 1996), pp. 19981-19985.
Bhugun et al., "Catalysis of the Electrochemical Reduction of Carbon Dioxide by Iron(0) Porphyrins: Synergystic Effect of Weak Brönsted Acids," J. Am. Chem. Soc., vol. 118, No. 7, 1996, pp. 1769-1776.
Cao et al., "The Electrocatalytic Reduction of Carbon Dioxide using Cobalt Tetrakis (4-trimethylammoniophenyl) Porphyrin Under High Pressure," Acta Chimica Sinica, vol. 4, No. 2, Jan. 1986, pp. 133-139, XP055124846.
Costentin et al., "A Local Proton Source Enhances $CO_2$ Electroreduction to CO by a Molecular Fe Catalyst," Science, vol. 338, No. 6103, Oct. 5, 2012, pp. 90-94 (Total 6 pages), XP055124797.
Costentin et al., "Catalysis of the Electrochemical Reduction of Carbon Dioxide," Chem. Soc. Rev., vol. 42, 2013 (Published Dec. 11, 2012 on http://pubs.rsc.org), pp. 2423-2436.
Costentin et al., "Proton-Coupled Electron Transfer Cleavage of Heavy-Atom Bonds in Electrocatalytic Processes. Cleavage of a C—O Bond in the Catalyzed Electrochemical Reduction of $CO_2$," J. Am. Chem. Soc., vol. 135, 2013 (Published May 21, 2013), pp. 9023-9031.
Dhanasekaran et al., "p-Terphenyl-Sensitized Photoreduction of $CO_2$ with Cobalt and Iron Porphyrins. Interaction between CO and Reduced Metalloporphyrins," J. Phys. Chem. A, Sep. 1999 (Published on web Sep. 4, 1999), vol. 103, No. 38, pp. 7742-7748, XP055124861.
Grodkowski et al., "Iron Porphyrin-Catalyzed Reduction of $CO_2$, Photochemical and Radiation Chemical Studies," J. Phys. Chem. A, vol. 101, No. 3, 1997 (Abstract published Jan. 1, 1997), pp. 248-254, XP055124862.
International Search Report (form PCT/ISA/210), dated Jul. 23, 2015, for International Application No. PCT/EP2015/059746.
Wuts et al., "Greene's Protective Groups in Organic Synthesis," Fourth Edition, John Wiley & Sons, Inc., Hoboken, New Jersey, 2007, pp. v-vii and ix- xxviii (Total 27 pages).
Yamazaki et al., "Effects of p-substituents on Electrochemical CO Oxidation by Rh Porphyrin-based Catalysts," Physical Chemistry Chemical Physics, vol. 12, No. 31, 2010 (Published Jun. 7, 2010), pp. 8968-8976, XP055124847.

* cited by examiner

PORPHYRIN MOLECULAR CATALYSTS FOR SELECTIVE ELECTROCHEMICAL REDUCTION OF $CO_2$ INTO CO

The present invention relates to novel porphyrins and complexes thereof with transition metals, in particular iron, preferably a Fe(III) or Fe(0) complex, and salts thereof. The invention in particular relates to the use of said complexes as catalysts for the selective electrochemical reduction of $CO_2$ into CO, electrochemical cells comprising them, and a method for selectively reducing electrochemically $CO_2$ into CO using said complexes.

Despite the increasingly frequent use of renewable energies to produce electricity avoiding concomitant production of $CO_2$, it is reasonable to consider that $CO_2$ emissions, in particular resulting from energy production, will remain high in the next decades. It thus appears necessary to find ways to capture $CO_2$ gas, either for storing or valorization purposes.

Indeed, $CO_2$ can also be seen, not as a waste, but on the contrary as a source of carbon. For example the promising production of synthetic fuels from $CO_2$ and water has been envisaged.

However, $CO_2$ exhibits low chemical reactivity: breaking its bonds requires an energy of 724 kJ/mol. Moreover, $CO_2$ electrochemical reduction to one electron occurs at a very negative potential, thus necessitating a high energy input, and leads to the formation of a highly energetic radical anion ($CO_2^{\delta-}$).. Catalysis thus appears mandatory in order to reduce $CO_2$ and drive the process to multi-electronic and multi-proton reduction process, in order to obtain thermodynamically stable molecules. In addition, direct electrochemical reduction of $CO_2$ at inert electrodes is poorly selective, yielding to formic acid in water, while it yields a mixture of oxalate, formate and carbon monoxide in low-acidity solvents such as DMF.

$CO_2$ electrochemical reduction thus requires catalytic activation in order to reduce the energy cost of processing, and increase the selectivity of the species formed in the reaction process.

Several low-oxidation state transition metal complexes have been proposed to serve as homogeneous catalyst for this reaction in non-aqueous solvents such as N,N'-dimethylformamide (DMF) or acetonitrile (see *Chem. Soc. Rev.* 2013, 42, 2423). Among them, electrochemically generated $Fe^0$ complexes have been shown to be good catalysts provided they are used in the presence of Brönsted or Lewis acids (see *J. Am. Chem. Soc.* 1996, 118, 1769; *J. Phys. Chem.* 1996, 100, 19981). More recent investigations have extended the range of Brönsted acids able to boost the catalysis of the $CO_2$-to-CO conversion by electrogenerated $Fe^0$TPP without degrading the selectivity of the reaction. They have also provided a detailed analysis of the reaction mechanism (see *J. Am. Chem. Soc.* 2013, 135, 9023).

This is notably the case with phenol, which gave rise to the idea of installing prepositioned phenol groups in the catalyst molecule 'CAT_ depicted below. The result was indeed a remarkably efficient and selective catalyst of the $CO_2$-to-CO conversion (see *Science* 2012, 338, 90).

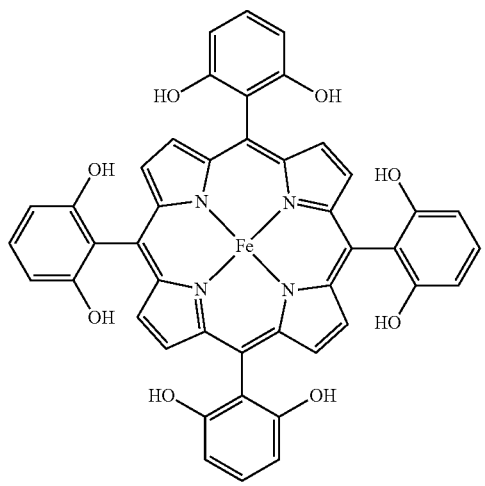

Structure of the "CAT" catalyst

Without wishing to be bound by theory, it seems that the role played by the internal phenol moieties is essential in the boosting of catalysis. They are thought to act both as H-bonding stabilizers of the initial $Fe(0)CO_2$ adduct and as high local concentration proton donors in the framework of the mechanism depicted in FIG. 1.

However, there remains a need for catalysts for the electrochemical reduction of $CO_2$ into CO based on iron porphyrins with even higher efficiency (i.e. high faradic yield, high Turnover Number (TON) and Turnover Frequency (TOF)), high selectivity and high stability, while operating at a lower overpotential (in absolute value).

SUMMARY OF THE INVENTION

Applicants thus propose replacing at least one of the electron-rich aryl groups by an aryl group comprising electron-withdrawing substituents, or an electron-withdrawing heteroaryl group.

Notwithstanding the fact that the inductive effect of said electron-withdrawing aryl or heteroaryl group was thought to ease the reduction of the molecule to the $Fe^0$ oxidation state, and thus to be favorable to catalysis in terms of overpotential, it was expected that this benefit would be blurred by a decrease of its reactivity toward $CO_2$. Indeed, the same inductive effect of the electron-withdrawing groups tends to decrease the electronic density on the $Fe^0$ complex, which was expected to render the formation of the initial $Fe^0CO_2$ adduct less favorable.

Surprisingly, this is not the case.

Indeed, the catalytic performances of the catalysts of the present invention, notably in terms of TOF and overpotential, are superior to known existing molecular catalysts for the electrochemical reduction of $CO_2$ gas into CO, in particular when compared to prior art catalyst CAT. Moreover the catalysts of the present invention exhibit high selectivity, typically as high as the selectivity exhibited by prior art catalyst CAT.

Therefore, in a first aspect, the present invention relates to a porphyrin of formula (I):

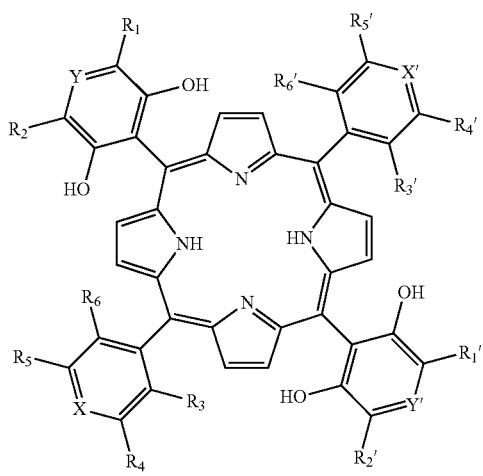

(I)

wherein $R^1$, $R^{1'}$, $R^2$ and $R^{2'}$ independently represent H, OH, F, $N^+R^7R^8R^9$, $C_1$-$C_4$ alkyl or $C_1$-$C_4$-alcohol, $R^3$, $R^{3'}$, $R^6$ and $R^{6'}$ are independently selected from the group consisting of H, OH, F and $C_1$-$C_4$-alcohol, $R^4$, $R^{4'}$, $R^5$, $R^{5'}$ are independently selected from the group consisting of H, OH, F, $C_1$-$C_4$ alkyl, $C_1$-$C_4$-alcohol, or $N^+R^7R^8R^9$, X and X' independently represent CH, CF, $CN^+R^7R^8R^9$, or $N^+R^7$, Y and Y' independently represent CH, CF, $CN^+R^7R^8R^9$, or $N^+R^7$, $R^7$, $R^8$ and $R^9$ independently of each other represent H or a $C_1$-$C_4$ alkyl group, provided that at least one of X, X', Y and Y' represents CF, $CN^+R^7R^8R^9$, or $N^+R^7$, or at least one of $R^3$, $R^{3'}$, $R^6$ and $R^{6'}$ represents F or at least one of $R^1$, $R^{1'}$, $R^2$, $R^{2'}$, $R^4$, $R^{4'}$, $R^5$, and $R^{5'}$ represents F or $N^+R^7R^8R^9$, and salts thereof.

In a second aspect, the present invention relates to complexes of said porphyrins of formula (I) with transition metals, in particular iron, preferably as Fe(III) or Fe(0) complex, and salts thereof.

In a third aspect, the present invention relates to the use of said complexes as catalysts for the selective electrochemical reduction of $CO_2$ into CO.

In a fourth aspect, the present invention relates to electrochemical cells comprising the complexes of the present invention.

In a further aspect, the present invention relates to a method of selectively reducing electrochemically $CO_2$ into CO using the complexes or the electrochemical cells of the invention.

In a further aspect, the present invention provides a method for preparing the porphyrins and corresponding complexes of the invention.

DETAILED DESCRIPTION OF THE INVENTION

Figure 1:
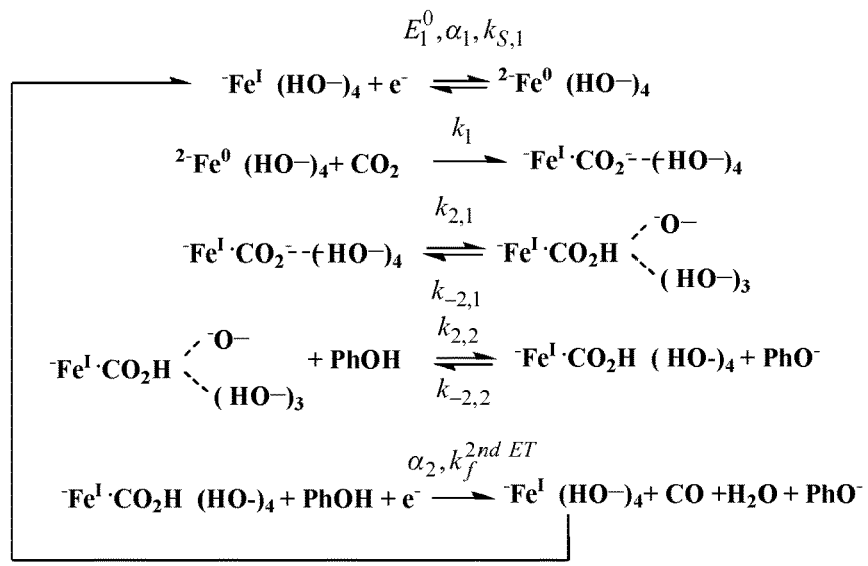
FIG. 1 represents a simplified reaction scheme for $CO_2$ reduction by iron(0) porphyrins bearing pendant acid groups into CO.

As used herein, the words "include," 'comprise, 'contain_, and their variants, are intended to be non-limiting, such that recitation of items in a list is not to the exclusion of other like items that may also be useful in the materials, compositions, devices, and methods of this invention.

According to the present invention, an alkyl is understood to mean a linear or branched, saturated hydrocarbon chain. Examples of $C_1$-$C_4$ alkyl are methyl, ethyl, n-propyl, i-propyl, n-butyl, s-butyl, t-butyl.

According to the present invention, a $C_1$-$C_4$ alcohol is understood to mean an alkyl substituted by at least one hydroxyl group. The $C_1$-$C_4$ alcohol may be linear or branched, and is saturated. Examples of C1-C4 alcohol are hydroxymethyl, 1-hydroxyethyl, 2-hydroxyethyl, 1-hydroxypropyl, 2-hydroxypropyl, 3-hydroxypropyl, 1-hydroxy-1-methylethyl, 2-hydroxy-1-methylethyl, 1-hydroxybutyl, 2-hydroxybutyl, 3-hydroxybutyl, 4-hydroxybutyl, 1-hydroxy-2-methylpropyl, 2-hydroxy-2-methylpropyl, 3-hydroxy-2-methylpropyl, 1-hydroxy-1-methylpropyl, 2-hydroxy-1-methylpropyl, 3-hydroxy-1-methylpropyl, (hydroxymethyl)-1-propyl, 1,2-dihydroxyethyl.

As used herein, 'overpotential (:)_ is understood as a potential difference between the thermodynamic reduction potential of the $CO_2$/CO couple ($E°_{CO2/CO}$) and the potential at which the reduction is experimentally observed (E), according to the following equation: $η = E°_{A/C} - E$.

As used herein, the 'TurnOver Number (TON)_ represents the number of moles of substrate that a mole of active catalyst can convert.

As used herein, the 'TurnOver Frequency (TOF)_ refers to the turnover per unit of time:

$$TOF = \frac{TON}{t},$$

with t representing the time of catalysis.

As used herein, '$TOF_0$ represents the TurnOver Frequency at zero overpotential. The value of $TOF_0$ is obtained from extrapolation of the TOF vs. overpotential curve at zero overpotential. The TOF vs. overpotential curve is obtained from the experimental measurement of the current density (I) as function of potential (E) using cyclic voltammetry. For example, in the case of a simple mechanism (i.e. if the chemical steps in the catalytic loop are equivalent to a single step characterized by an apparent catalytic constant) the following relationship can be used:

$$TOF = \frac{I}{F\sqrt{\frac{D}{k_{cat}}C^0_{cat}}}$$

with D being the diffusion coefficient of the catalyst, $C^0_{cat}$ being its concentration in solution and $k_{cat}$ the catalytic rate constant. The value of $TOF_0$ is preferably obtained from extrapolation of the TOF vs. overpotential curve at zero overpotential. Said TOF vs. overpotential curve is for instance obtained such as described in Chem ElectroChem (in press, DOI: 10.1002/celc.201490020), or calculated as detailed in Costentin et al, Science 338, 90 (2012).

As used herein, the acronym NHE is understood as 'Normal Hydrogen Electrode_.

As used herein, the acronym SCE is understood as 'Standard Calomel Electrode_. Electrolysis is for instance performed in an electrochemical cell, which typically comprise at least:

an electrolyte solution comprising the solvent, a supporting electrolyte as a salt, and the substrate;

a power supply providing the energy necessary to trigger the electrochemical reactions involving the substrate; and two electrodes, i.e. electrical conductors providing a physical interface between the electrical circuit and the solution.

As used herein, the 'faradic yield of an electrochemical cell_ aimed at producing CO (or $H_2$) gas through electrochemical reduction of $CO_2$ gas is the ratio of the amount of electrons (in Coulomb) used to produce CO (or $H_2$) gas relative to the amount of electrons (in Coulomb) furnished to the electrochemical system by the external electric source. The faradic yield is expressed in %.

According to the present invention, a 'homogeneous catalyst_ is a catalyst which is contained in the same phase as the reactants. In contrast, a heterogeneous catalyst is contained in a phase which differs from the phase of the reactants. Therefore, in the present invention, a 'homogeneous catalyst_ is soluble in the electrochemical cell solution. In particular, the homogeneous catalysts of the invention are soluble in DMF (N,N-dimethylformamide), ACN (acetonitrile) and mixtures thereof, in particular mixtures of ACN and water, and mixtures of DMF and water.

First, the present invention concerns a porphyrin of formula (I):

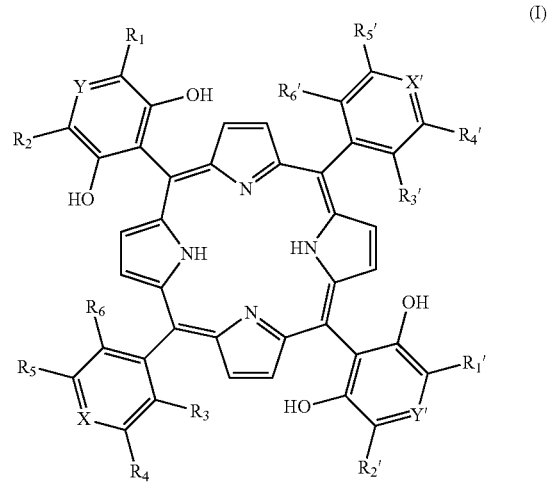

wherein $R^1$, $R^{1\prime}$, $R^2$ and $R^{2\prime}$ independently represent H, OH, F, $N^+R^7R^8R^9$, $C_1$-$C_4$ alkyl or $C_1$-$C_4$-alcohol, $R^3$, $R^{3\prime}$, $R^6$ and $R^{6\prime}$ are independently selected from the group consisting of H, OH, F and $C_1$-$C_4$-alcohol, $R^4$, $R^{4\prime}$, $R^5$, $R^{5\prime}$ are independently selected from the group consisting of H, OH, F, $C_1$-$C_4$ alkyl, $C_1$-$C_4$-alcohol, or $N^+R^7R^8R^9$, X and X' independently represent CH, CF, $CN^+R^7R^8R^9$, or $N^+R^7$, Y and Y' independently represent CH, CF, $CN^+R^7R^8R^9$, or $N^+R^7$, $R^7$, $R^8$ and $R^9$ independently of each other represent H or a $C_1$-$C_4$ alkyl group, provided that at least one of X, X', Y and Y', preferably X or X', represents CF, $CN^+R^7R^8R^9$, or $N^+R^7$, or at least one of $R^3$, $R^{3\prime}$, $R^6$ and $R^{6\prime}$, represents F, or at least one of $R^1$, $R^{1\prime}$, $R^2$, $R^{2\prime}$, $R^4$, $R^{4\prime}$, $R^5$, and $R^{5\prime}$ represents F or $N^+R^7R^8R^9$, and salts thereof, in particular chlorides thereof.

The porphyrins of formula (I) may be isolated as salts with an organic or inorganic anion(s), or mixtures thereof. Anions are preferably inorganic anions because they are more stable when used according to the invention. Preferred inorganic anions are chloride, perchlorate, $PF_6^-$. More preferably, the anion is chloride.

The present invention also contemplates solvates of the porphyrins of formula (I), in particular hydrates thereof.

Preferably, at least one of X, X', Y, or Y', more preferably at least X and X', represent CF, $CN^+R^7R^8R^9$, or $N^+R^7$, or at least one of $R^1$, $R^{1\prime}$, $R^2$, $R^{2\prime}$ $R^4$, $R^{4\prime}$, $R^5$, and $R^{5\prime}$ represents F or $N^+R^7R^8R^9$, with $R^7$, $R^8$ and $R^9$ as described above and below.

Preferably, $R^7$, $R^8$ and $R^9$ are independently selected from $C_1$-$C_4$ alkyl. Compared to porphyrins wherein $R^7$, $R^8$ and $R^9$ represent H, porphyrins wherein $R^7$, $R^8$ and $R^9$ represent $C^1$-$C^4$ alkyl enhance CO production over $H_2$ production.

Advantageously, $R^3$ is identical to $R^{3\prime}$, $R^4$ is identical to $R^{4\prime}$, $R^5$ is identical to $R^{5\prime}$, and $R^6$ is identical to $R^{6\prime}$. Advantageously, also, $R^1$ is identical to $R^{1\prime}$, and $R^2$ is identical to $R^{2\prime}$.

In a preferred embodiment, X and X' are identical. In this embodiment, advantageously, $R^3$ is identical to $R^{3\prime}$, $R^4$ is identical to $R^{4\prime}$, $R^5$ is identical to $R^{5\prime}$, and $R^6$ is identical to $R^{6\prime}$. Therefore, in this embodiment the porphyrin is preferably of formula (II):

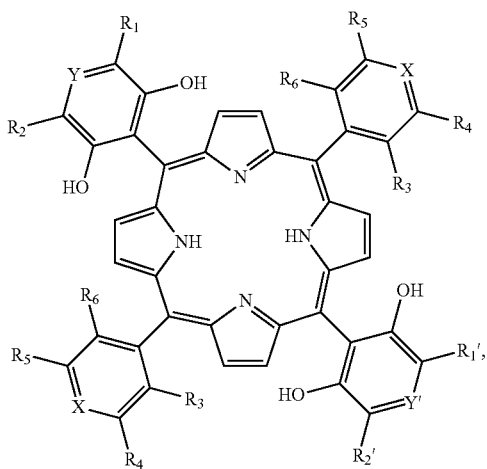

(II)

wherein $R^3$, $R^4$, $R^5$, $R^6$ and X are as described above and below, and $R^1$, $R^1$, $R^2$, $R^2$, Y and Y are as described above and below, and are preferably identical.

Preferably, in the porphyrin of formula (II), at least one of X, Y, or Y represents CF, $CN^+R^7R^8R^9$, or $N^+R^7$, or at least one of $R^1$, $R^1$, $R^2$, $R^2$ $R^4$ and $R^5$ represents $N^+R^7R^8R^9$. Advantageously, also, $R^1$ is identical to $R^1$, $R^2$ is identical to $R^2$. Preferably, Y and Y are also identical. Therefore, in a particularly preferred embodiment, the porphyrin is of formula (III):

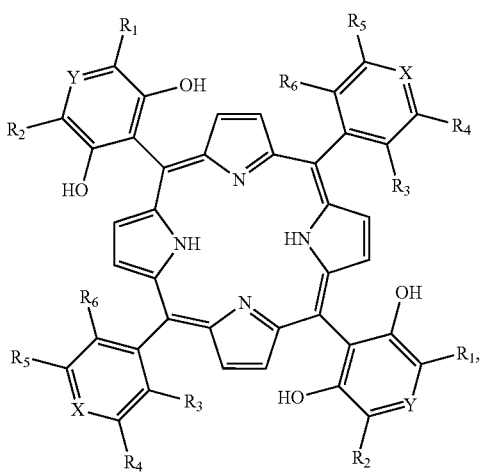

(III)

wherein $R^1$, $R^2$, $R^3$, $R^4$, $R^5$, $R^6$, X and Y are as described above and below, and at least one of X, or Y represents CF, $CN^+R^7R^8R^9$, or $N^+R^7$, or at least one of $R^1$, $R^2$, $R^4$ and $R^5$ represents $N^+R^7R^8R^9$, wherein $R^7$, $R^8$ and $R^9$ are as described above or below, and preferably represent a methyl group.

In a first embodiment, $R^4$, $R^4$, $R^5$, and $R^5$ are independently selected from the group consisting of H, OH, F, $C_1$-$C_4$ alkyl and $C_1$-$C_4$ alcohol, preferably OH, H or F; and $R^3$, $R^3$, $R^6$ and $R^6$ are independently selected from the group consisting of H, OH, F and $C_1$-$C_4$-alcohol, provided that at least one, preferably at least four, of $R^3$, $R^3$, $R^4$, $R^4$, $R^5$, $R^5$, $R^6$ and $R^6$ is F.

Advantageously, in this embodiment, X and X independently represent CH or CF, preferably CF. Particularly advantageously, in this embodiment, X is identical to X, $R^3$ is identical to $R^3$, $R^4$ is identical to $R^4$, $R^5$ is identical to $R^5$, and $R^6$ is identical to $R^6$. More advantageously, $R^3$, $R^3$, $R^6$, and $R^6$ all represent F and X and X represent CF. Even more advantageously, in this embodiment, $R^3$, $R^3$, $R^4$, $R^4$, $R^5$, $R^5$, $R^6$, $R^6$ all represent F and X and X represent CF. Preferably, in this embodiment, Y and Y represent CH or CF, more preferably CH. Advantageously, Y is identical to Y, $R^1$ is identical to $R^1$ and $R^2$ is identical to $R^2$. Even more advantageously, Y, Y represent CH and $R^1$, $R^1$, $R^2$, $R^2$ all represent H.

In particular, in this first embodiment, the porphyrin of the invention is:

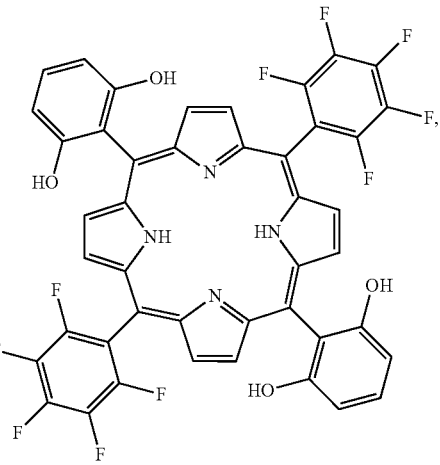

The iron complex of this perfluorinated prophyrin is called 'FCAT_.

In a second embodiment, Y, Y, X and X are independently selected from CH and $CN^+R^7R^8R^9$, with $R^7$, $R^8$ and $R^9$ as described above and below, and $R^1$, $R^1$, $R^2$, $R^2$, $R^4$, $R^4$, $R^5$, and $R^5$, are independently selected from H, OH, $C_1$-$C_4$ alkyl, $C_1$-$C_4$-alcohol, or $N^+R^7R^8R^9$ provided that at least one of Y, Y, X and X is $CN^+R^7R^8R^9$ or at least one of $R^1$, $R^1$, $R^2$, $R^2$, $R^4$, $R^4$, $R^5$, and $R^5$ is $N^+R^7R^8R^9$. Preferably, $R^7$, $R^8$ and $R^9$ are independently of each other selected from methyl and ethyl groups, more preferably they all are methyl groups. Advantageously, in this embodiment, X is identical to X, $R^3$ is identical to $R^3$, $R^4$ is identical to $R^4$, $R^5$ is identical to $R^5$, and $R^6$ is identical to $R^6$. Even more advantageously, in this second embodiment, $R^3$, $R^3$, $R^6$, $R^6$ are independently selected from H, OH and F, preferably $R^3$, $R^3$, $R^6$, $R^6$ all represent H and $R^4$, $R^4$, $R^5$, $R^5$ are independently selected from H, $N^+R^7R^8R^9$ and F, preferably $R^4$, $R^4$, $R^5$, $R^5$ all represent H or $N^+R^7R^8R^9$.

Preferably, in this embodiment, Y and Y are independently selected from CH and $CN^+R^7R^8R^9$, with $R^7$, $R^8$ and $R^9$ as described above and preferably representing a methyl or ethyl group, even more preferably a methyl group. Advantageously, Y is identical to Y, $R^1$ is identical to $R^1$ and $R^2$ is identical to $R^2$. Even more advantageously, $R^1$, $R^1$, $R^2$, $R^2$ all represent H or $N^+R^7R^8R^9$. In particular, in this second embodiment, the porphyrin of the invention is:

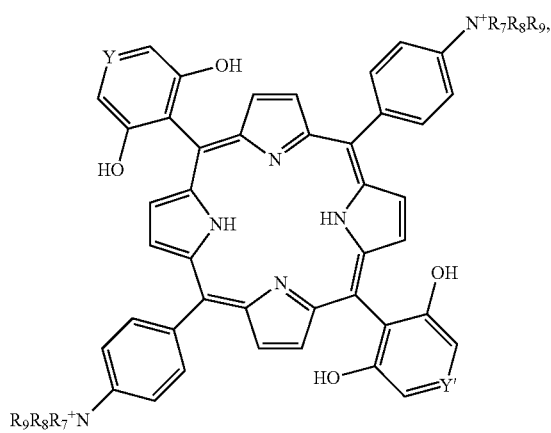

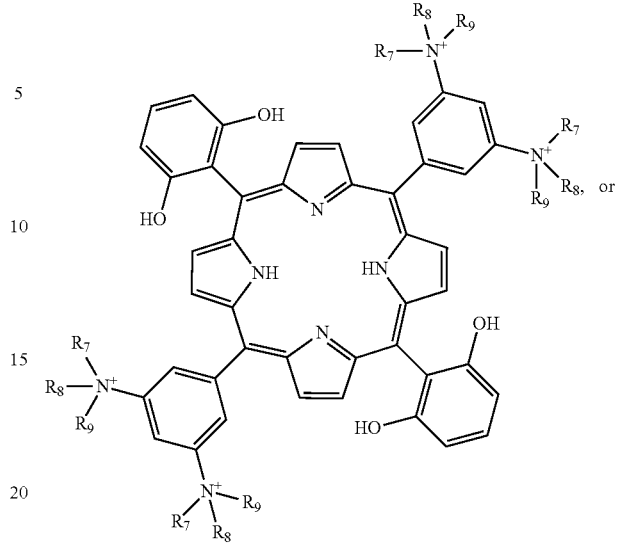

and salts thereof, wherein Y, Y, $R^7$, $R^8$ and $R^9$ are as described above and below.

In this second embodiment, the porphyrin of formula (I) is at least a di-cation. Preferably, it is a di-cation. In any case, this porphyrin is thus preferably isolated as a salt, with organic or inorganic anions or mixtures thereof.

Even more preferably, in this second embodiment, the porphyrin of the invention is:

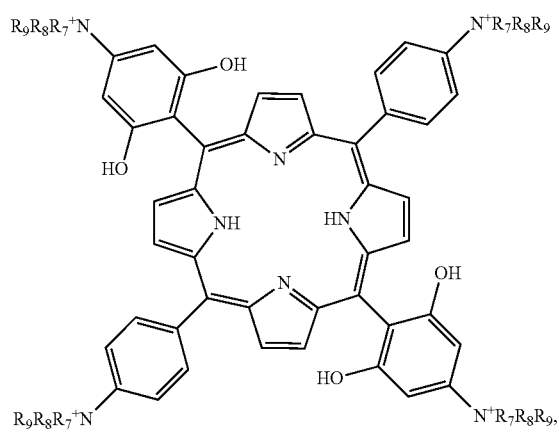

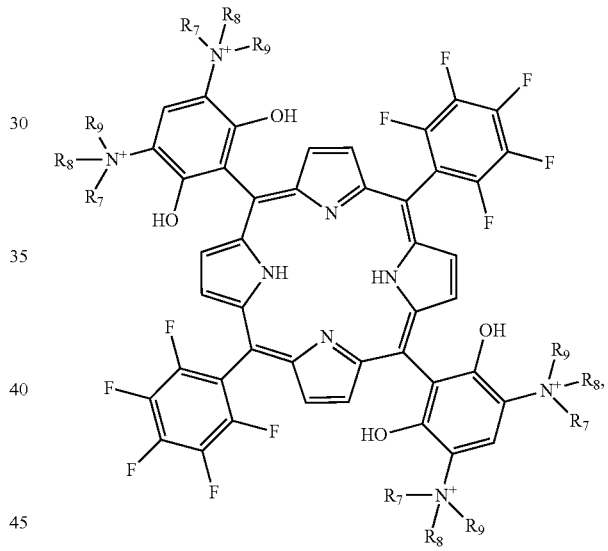

and salts thereof, wherein $R^7$, $R^8$ and $R^9$ are as described above and below, and preferably represent a methyl group. In this particular case, the porphyrin of formula (I) is a tetra-cation, which is thus preferably isolated as a salt, with an organic or inorganic anion(s), or mixtures thereof.

Also, in this second embodiment, the porphyrin of the invention may be:

and salts thereof, wherein $R^7$, $R^8$ and $R^9$ are as described above and below, and preferably represent a methyl group. In this particular case, the porphyrin of formula (I) is a tetra-cation, which is thus preferably isolated as a salt, with an organic or inorganic anion(s), or mixtures thereof.

In this second embodiment, anions are preferably inorganic anions because they are more stable when used according to the invention. Preferred inorganic anions are chloride, perchlorate, $PF_6^-$. More preferably, the anion is chloride.

In a third embodiment, X and X are independently selected from CH and $N^+R^7$, with $R^7$ as described above, in particular representing a methyl group, provided that at least one of X and X is $N^+R^7$. Preferably, $R^7$ is selected from methyl and ethyl groups, more preferably it is a methyl group.

Advantageously, in this embodiment, X is identical to X, $R^3$ is identical to $R^3$, $R^4$ is identical to $R^4$, $R^5$ is identical to $R^5$, and $R^6$ is identical to $R^6$. Even more advantageously, in this third embodiment, $R^3$, $R^3$, $R^4$, $R^4$, $R^5$, $R^5$, $R^6$, $R^6$ are independently selected from H and F, preferably they all represent H. In this third embodiment, $R^7$ is as described above, and preferably represents a methyl group.

Preferably, in this embodiment, Y and Y are independently selected from CH and $N^+R^7$, with $R^7$ as described above and preferably representing a methyl group. Advantageously, Y is identical to Y, $R^1$ is identical to $R^1$ and $R^2$ is identical to $R^2$. Even more advantageously, $R^1$, $R^1$, $R^2$, $R^2$ all represent H and Y, Y represent CH. In particular, in this third embodiment, the porphyrin of the invention is:

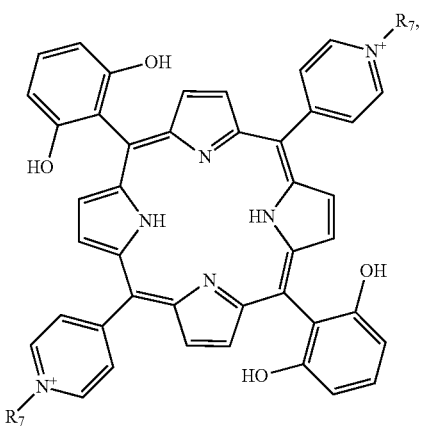

and salts thereof, wherein $R^7$ is as described above, and preferably represents a methyl group.

In this third embodiment, the porphyrin of formula (I) is at least a di-cation. Preferably, it is a di-cation. In any case, this porphyrin is thus preferably isolated as a salt, with organic or inorganic anions or mixtures thereof.

In this third embodiment, anions are preferably inorganic anions because they are more stable when used according to the invention. Preferred inorganic anions are chloride, perchlorate and $PF_6^-$.

More preferably, the anion is chloride.

Porphyrins of the invention according to the above second and third embodiments show an improved solubility in water.

The present invention further relates to complexes of said porphyrins of formula (I) with transition metals, and salts thereof. Preferred examples of transition metals are Fe, Co, in particular iron, preferably the complex is a Fe(III) or Fe(0) complex, and salts thereof.

In some instances, the complexes of the invention may be such that the metal ion is coordinated in the center of the porphyrin by the nitrogen atoms, which have thus lost their protons.

The complexes of the invention are typically synthesized and introduced in an electrochemical cell as the chloride of the Fe(III) complex. However, during the electrochemical process, at least a portion of the transition metal species (in particular iron species) is cyclically oxidized and reduced. That is, the oxidation state of at least a portion of the transition metal species (in particular iron species) involved in the dynamic equilibrium is repeatedly changed during the electrochemical process. Typically, in the present invention, the iron atom is first reduced to Fe(0) and all oxidation states Fe(0), Fe(I) and Fe(II) are successively involved during the catalytic cycle of the $CO_2$ reduction into CO.

The complexes of the invention are preferably of formula (IV):

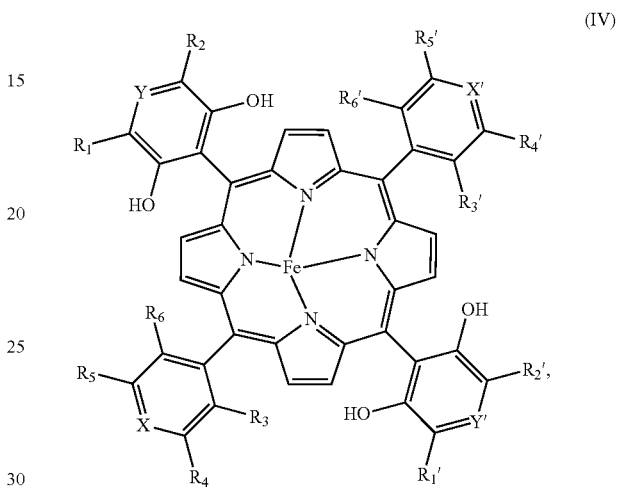

or preferably of formula (V)

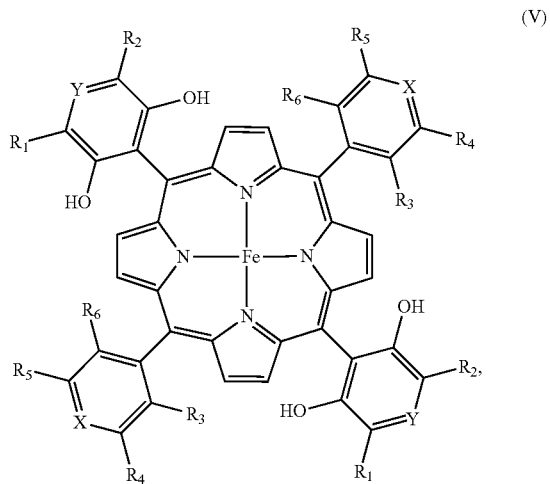

wherein $R^1$, $R^1$, $R^2$, $R^2$, $R^3$, $R^3$, $R^4$, $R^4$, $R^5$, $R^5$, $R^6$, $R^6$, X, X, Y and Y are as described herein.

It is thus understood in the Fe complexes of the porphyrins of formula (IV) or (V), Fe may represent either Fe(0), Fe(I), Fe(II) or Fe(III). Moreover, the complexes may further comprise inert ligands, in particular to provide an electronically neutral species, or such as labile molecules of solvent. However, it is noted that the catalytic cycle of the invention involves mainly the Fe(0)/Fe(II) couples.

In particular, the complex of the invention is:
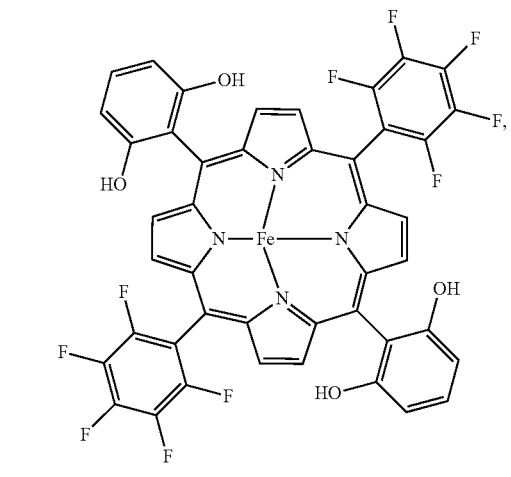
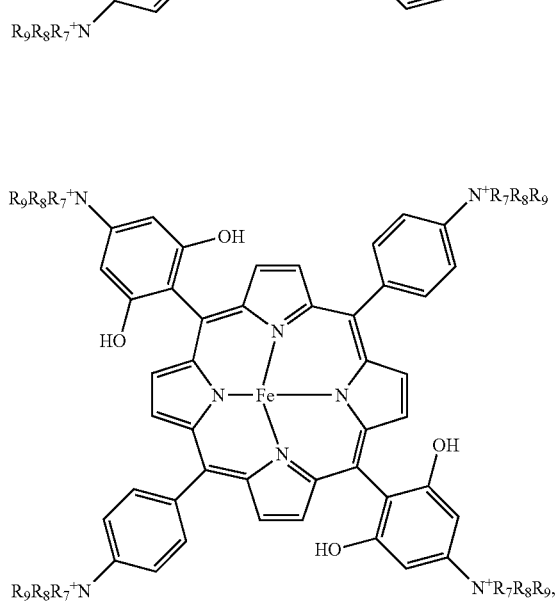
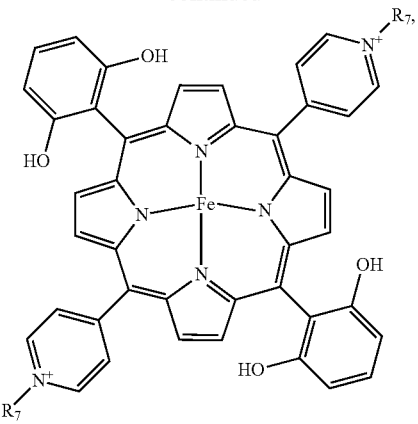
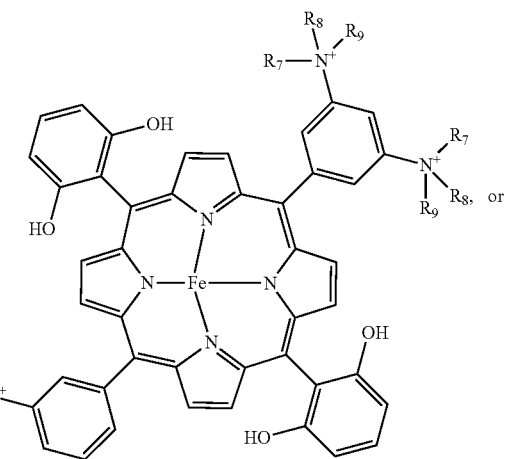
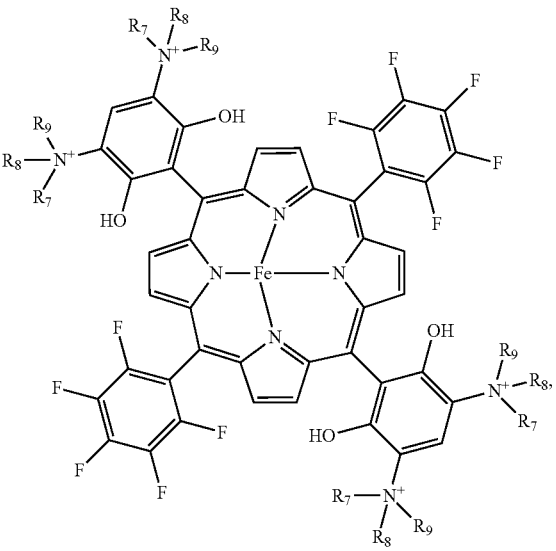
wherein $R^7$, $R^8$ and $R^9$ are as described above, preferably a methyl group.

In a particularly preferred embodiment, the complex of the invention is

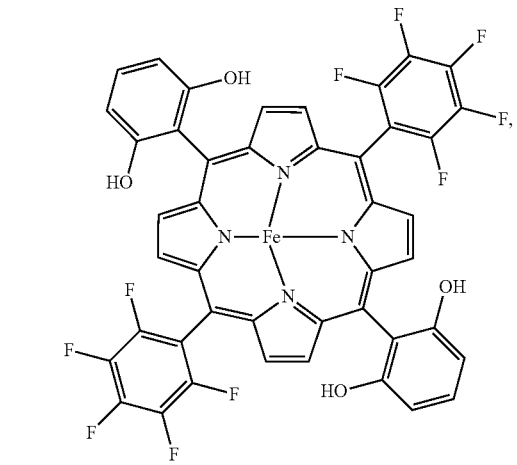

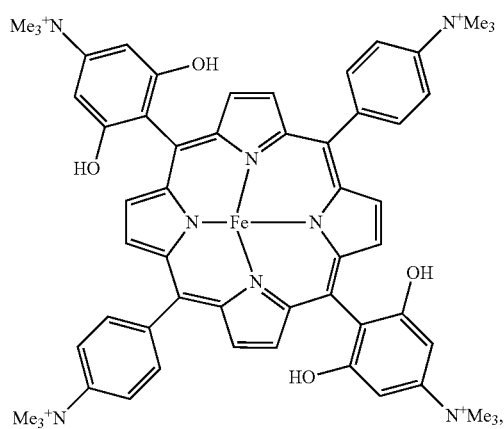

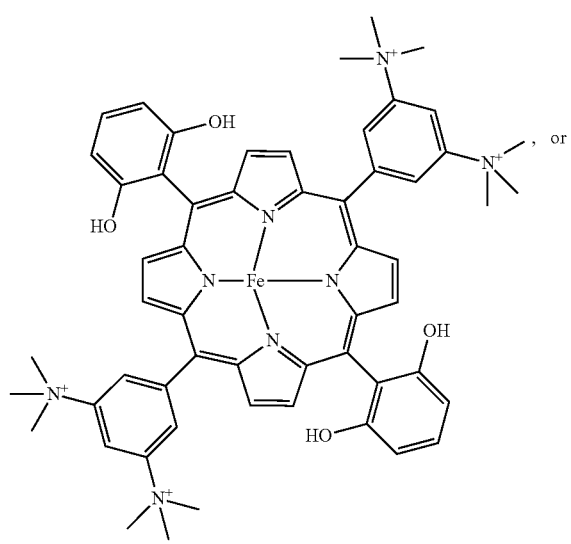

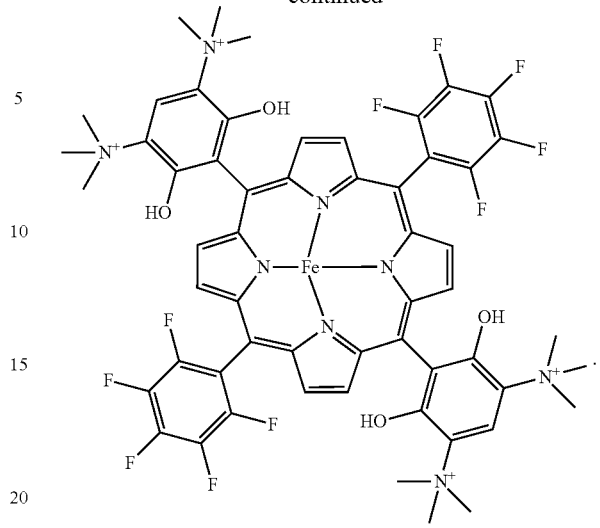

The complexes of the invention, in particular the complexes of formula (IV) or (V), preferably have a $TOF_0$ greater than $10^{-10}$ s$^{-1}$, preferably greater than $10^{-8}$ s$^{-1}$, more preferably greater than $10^{-6}$ s$^{-1}$.

The present invention further concerns the use of said complexes as catalysts for the electrochemical reduction of $CO_2$ into CO. Despite that depending on the experimental conditions $H_2$ production can be promoted, in the use of the invention, the electrochemical reduction of $CO_2$ into CO may advantageously be selective. In particular, no formation of formic acid or formate is observed.

Advantageously, the complexes of the present invention are used in combination with a proton donor, advantageously with a pK value in DMF of between 18 and 31, in particular selected from the group consisting of water ($H_2O$), trifluoroethanol, phenol and acetic acid, advantageously $H_2O$ or phenol. Without wishing to be bound by theory, if the proton donor is too acidic, the complex is degraded too quickly in the reaction medium, and the selectivity of the reaction may be affected. In particular, $H_2$ formation may be observed.

Advantageously, when the complexes of the present invention are used in combination with a proton donor, said proton donor is used in a concentration of between 100 mM and 5M, preferably between 100 mM and 3M, even more preferably between 1M and 3M.

The complexes of the present invention are advantageously used as homogenous catalysts.

The present invention further relates to electrochemical cells comprising the complexes of the present invention.

The electrochemical cell of the present invention typically comprises at least:
- an electrolyte solution comprising the solvent, a supporting electrolyte such as a salt, and the substrate, in the present case $CO_2$;
- a power supply providing the energy necessary to trigger the electrochemical reactions involving the substrate; and
- two electrodes, i.e. electrical conductors providing a physical interface between the electrical circuit and the solution.

The solvent is preferably an organic medium, advantageously selected from DMF (dimethylformamide) or ACN (acetonitrile), and mixtures thereof.

Advantageously, the electrolyte solution comprises DMF (dimethylformamide) or ACN (acetonitrile). The electrolyte solution may further contain salts as the supporting electrolyte, such as n-NBu$_4$PF$_6$, or NaCl for example. The electrolyte solution may further contain additives such as Et$_2$NCO$_2$CH$_3$ for instance.

Preferably, the electrolyte solution further comprises a proton donor, advantageously with a pKa value in DMF of between 18 and 31, in particular selected from the group consisting of water (H$_2$O), trifluoroethanol, phenol and acetic acid, advantageously H$_2$O or phenol. Advantageously, when a proton donor is used, said proton donor is used in a concentration of between 100 mM and 5M, preferably between 100 mM and 3M, even more preferably between 1M and 3M. In some embodiments, the electrolyte solution is a solution of phenol or water in DMF, preferably a 0-5.0 M solution of water or phenol in DMF, more preferably 0-2.5 M solution of water or phenol in DMF, even more preferably 1.0-2.0 M solution of water or phenol in DMF, and may contain additives such as salts.

Advantageously, the electrolyte solution comprises a complex of the invention, in particular of formula (III) as defined above.

In one embodiment, the complex of the invention, in particular of formula (IV) as defined above, is in a concentration, in the electrolyte solution, of between 0.0005 and 0.01 M, preferably 0.001 M.

In one embodiment, the electrochemical cell of the invention is saturated with CO$_2$ gas, that is to say, both the atmosphere and the electrolyte solution are saturated with CO$_2$.

The power source may comprise one or more of power supplies (e.g., batteries and a photovoltaic cell). The voltage applied may be AC or DC.

Advantageously, the anode is a conductive electrode. Preferably, the anode is a carbon or platinum electrode. More preferably, the anode is a platinum electrode, in particular a platinum wire.

Advantageously, the cathode is a carbon, mercury, electrode. Preferably, it is a carbon electrode, such as a carbon crucible or glassy carbon.

In a particular embodiment, the electrochemical cell further comprises a third electrode, preferably a reference electrode such as a standard calomel electrode or a silver chloride electrode.

In one embodiment the electrochemical cell comprises one compartment.

In another embodiment the electrochemical cell comprises several compartments, preferably two compartments. In particular, one compartment contains the anode, and this compartment is bridge separated from the cathodic compartment by a glass frit. In this embodiment, the anodic and cathodic compartments contain two different electrolytes. Preferably, the electrolyte of the cathodic compartment is a solution of Et$_2$NCO$_2$CH$_3$ and 0.1 M n-NBu$_4$PF$_6$ in DMF. Advantageously, in this case Et$_2$NCO$_2$CH$_3$ is in a concentration of between 0.01 and 1 M, preferably 0.1 and 0.5 M, even more preferably 0.4 M, and n-NBu$_4$PF$_6$ is in a concentration of between 0.01 and 1 M, preferably 0.01 and 0.5 M, even more preferably 0.1 M.

The present invention further concerns a method comprising performing electrochemical reduction of CO$_2$ using the electrochemical cell of the present invention, thereby producing CO gas.

Advantageously, the electrochemical reduction is carried out in the presence of a proton donor, advantageously with a pK value in DMF of between 18 and 31, in particular selected from the group consisting of water (H$_2$O), trifluoroethanol, phenol and acetic acid, advantageously H$_2$O or phenol. Said proton donor is advantageously comprised in the electrolyte solution of the electrochemical cell, and advantageously in a concentration of between 100 mM and 5M, preferably between 100 mM and 3M, even more preferably between 1M and 3M. Preferably, DMF or ACN is the solvent of the electrolyte solution, which may further contain additives such as salts.

The power source may comprise one or more of power supplies (e.g., batteries and a photovoltaic cell). The voltage applied may be AC (alternative) or DC (direct).

Advantageously, the potential applied to the cathode is between −2.5 V and −0.5 V versus NHE, more advantageously between −2.0 V and −0.5 V versus NHE, more advantageously between −1.5 V and −0.8 V versus NHE, more advantageously between −1.3 V and −1.0 V versus NHE.

Advantageously, the intensity applied to the cathode is between 2 and 5 A/m$^2$, more preferably between 2.5 and 4 A/m$^2$, even more preferably between 3 and 3.5 A/m$^2$.

Preferably, the method of the invention is carried out at a temperature between 15 and 30° C., more preferably, between 20 and 25° C.

The faradic yield of the method is preferably comprised between 80% and 99%, in particular between 84% and 99%, or between 90% and 99%, or more preferably between 94 and 99%. Therefore, the method of the present invention allows for a clean conversion of CO$_2$ into CO, producing only minimal amounts of undesired byproducts. In general, no formation of formic acid, formate is observed.

In one embodiment, the electrochemical cell is used as a closed system regarding CO$_2$ gas. In a yet preferred embodiment, the method of the invention is carried out with a stream of CO$_2$. Preferably, said stream allows for saturating the electrolyte solution as well as the electrochemical cell atmosphere. It is of note that CO is typically not soluble in the electrolyte solution, so that it is collected directly as a gas.

The present invention further relates to a method of selectively reducing electrochemically CO$_2$ into CO using a complex of the invention, in particular of formula (III) as defined above, or the electrochemical cells of the invention.

Advantageously, the electrochemical reduction is carried out in the presence of a proton donor, advantageously with a pK value in DMF of between 18 and 31, preferably selected from the group consisting of water (H$_2$O), trifluoroethanol, phenol and acetic acid, even more advantageously H$_2$O or phenol. Said proton donor is advantageously comprised in the electrolyte solution of the electrochemical cell, and advantageously in a concentration of between 100 mM and 5M, preferably between 100 mM and 3M, even more preferably between 1M and 3M. Preferably, DMF or ACN is the solvent of the electrolyte solution, which may further contain additives such as salts.

The power source may comprise one or more of power supplies (e.g., batteries and a photovoltaic cell). The voltage applied may be AC (alternative) or DC (direct).

Advantageously, the potential applied to the cathode is between −2.5 V and −0.5 V versus NHE, more advantageously between −2.0 V and −0.5 V versus NHE, more advantageously between −1.5 V and −0.8 V versus NHE, more advantageously between −1.3 V and −1.0 V versus NHE.

Advantageously, the intensity applied to the cathode is between 2 and 5 A/m$^2$, more preferably between 2.5 and 4 A/m$^2$, even more preferably between 3 and 3.5 A/m$^2$.

Preferably, the method of the invention is carried out at a temperature between 15 and 30° C., more preferably, between 20 and 25° C.

The faradic yield of the method is preferably comprised between 80% and 99%, in particular between 84% and 99%, or between 90% and 99%, or more preferably between 94 and 99%. Therefore, the method of the present invention allows for a clean conversion of $CO_2$ into CO, producing only minimal amounts of undesired byproducts. In general, no formation of formic acid, formate is observed.

In one embodiment, the electrochemical cell is used as a closed system regarding $CO_2$ gas. In a yet preferred embodiment, the method of the invention is carried out with a stream of $CO_2$. Preferably, said stream allows for saturating the electrolyte solution as well as the electrochemical cell atmosphere. It is of note that CO is typically not soluble in the electrolyte solution, so that it is generally collected directly as a gas.

The present invention further relates to a method of preparing the complexes of the invention, in particular of formula (IV) as defined above, from the porphyrins of formula (I) as described above.

The method of the invention comprises reacting a salt of iron(II), in particular a dihalide of iron (II) such as $FeBr_2$ with the porphyrin of formula (I), preferably in the presence of a base, thus yielding the iron (III) complex of formula (IV), in particular as depicted in the reaction scheme below:

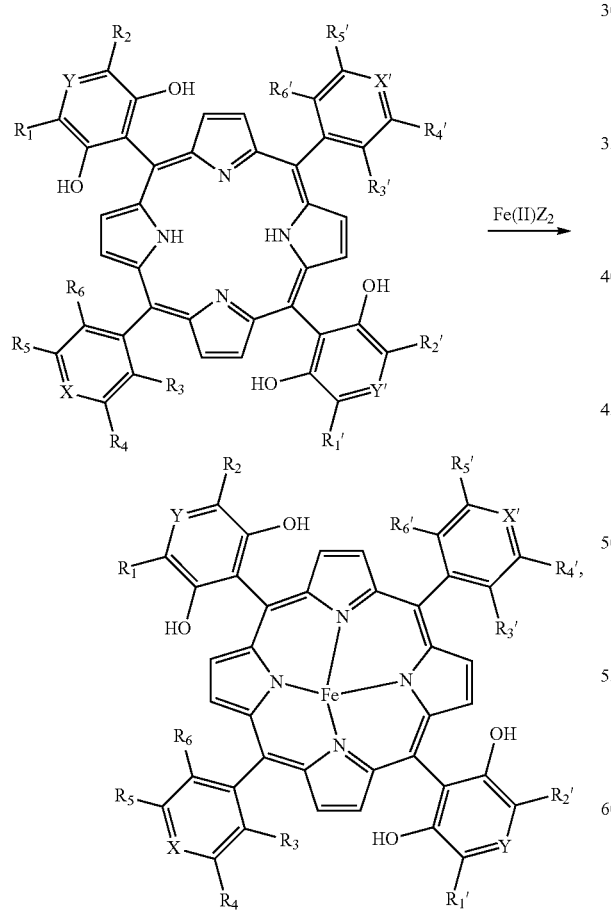

wherein Z represents a monoanion, in particular a halide such as chloride or bromide, preferably bromide.

This reaction is preferentially carried out in a protic solvent such as an alcohol, preferably methanol, ethanol, isopropanol or butanol, even more preferably methanol.

This reaction is advantageously carried out at a temperature comprised between 25° C. and the boiling point of the solvent (at atmospheric pressure), preferably between 40° C. and the boiling point of the solvent (at atmospheric pressure), even more preferably between 40° C. and 60° C.

Advantageously, the reaction comprises a further step of evaporating the solvent, then taking up the residue in a solvent which is not miscible in water, and washing the organic phase thus obtained with an acidic solution, preferably an aqueous HCl solution, more preferably diluted aqueous HCl solution.

The complexes of formula (IV), especially wherein $R^4$, $R^4$, $R^5$, and $R^5$ are independently H, OH, F, $C_1$-$C_4$ alkyl or $C_1$-$C_4$ alcohol, and wherein X, X, Y and Y independently represent CH or CF may be purified by column chromatography, for instance on silica gel.

When at least one of X, X, Y, Y, $R^4$, $R^4$, $R^5$, and $R^5$ represents $N^+R^7R^8R^9$, or X or X represent $NR^7$, with $R^7$, $R^8$ and $R^9$ as described above, then the complexes of formula (IV) may be purified using ion exchange resins.

The present invention further concerns a method of preparing the porphyrins of formula (I), (II) and (III) as defined above.

In particular, the porphyrins of formula (III), notably wherein X and Y are independently CH or CF and $R^4$, $R^4$, $R^5$, $R^5$, are independently H, OH, F, $C_1$-$C_4$ alkyl or $C_1$-$C_4$ alcohol, may be prepared following the reaction scheme depicted below:

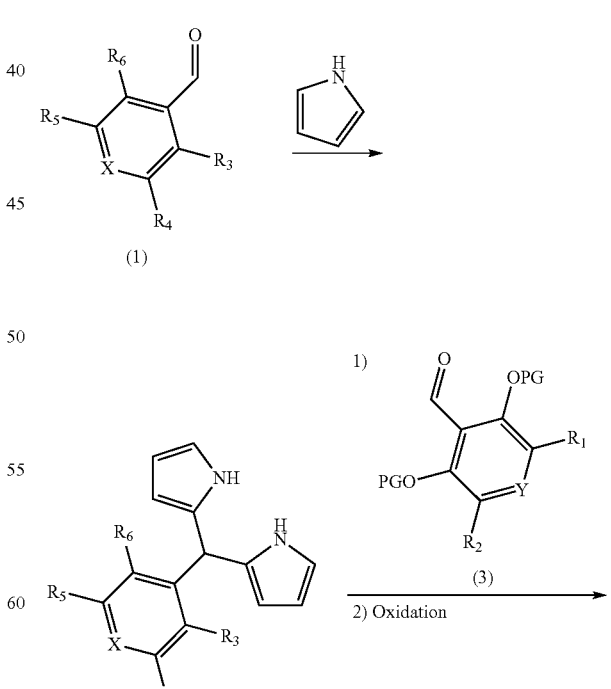

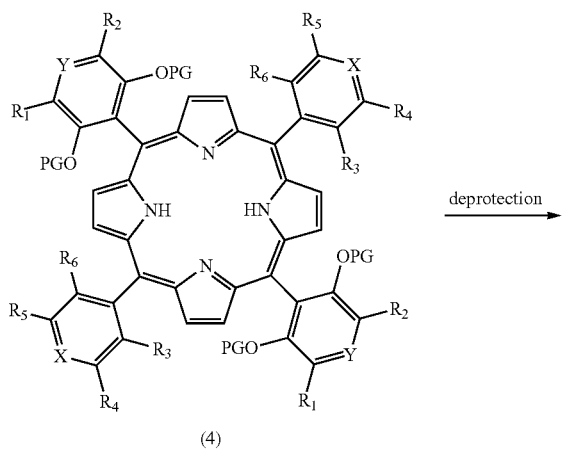

(4)

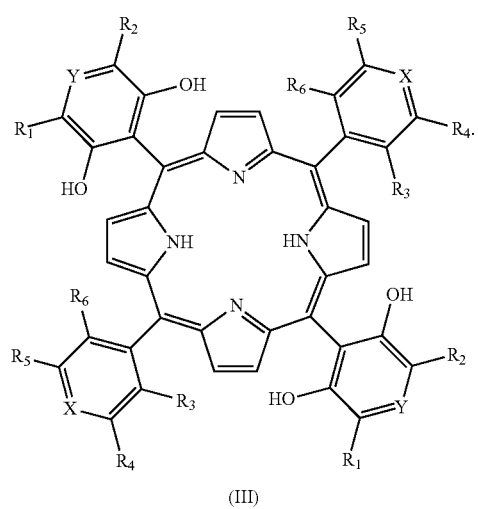

(III)

In a first step, substituted aryl aldehyde (1) is condensed with pyrrole leading to dipyrromethane (2). In this first step, at least two equivalents of pyrrole are used. Preferably, pyrrole, advantageously freshly distilled, is used as the solvent. Advantageously, the condensation is carried out under acidic conditions. Therefore, preferably, a carboxylic acid is used in sub-stoichiometric or catalytic amounts, i.e. in 1 to 20 mol %, for instance in 2 to 10 mol %.

Dipyrromethane (2) is then condensed with aldehyde (3), thus providing a tetracyclic intermediate, which is then oxidized to yield porphyrin (4). In other words, dipyrromethane (2) is then condensed with aldehyde (3), and thus subjected to oxidative conditions, thus yielding porphyrin (4). The oxidation substep is preferably carried out using 2,3-dichloro-5,6-dicyanobenzoquinone (DDQ).

In aldehyde (3), PG stands for Protecting Group. Said PG group is a suitable phenoxy protecting group, preferably selected from the suitable phenoxy protecting groups listed as such in Greene's Protective Groups in Organic Synthesis, Fourth Edition (Peter G. M. Wuts, Theodora W. Greene, John Wiley & Sons, Inc, 2007, ISBN 9780471697541). For instance, PG is a $C_1$-$C_4$ alkyl group, preferably a methyl group.

The following deprotection step is carried out in any suitable manner according to the nature of the PG protecting group, as described for instance in Greene's Protective Groups in Organic Synthesis, Fourth Edition cited above.

For instance, when PG represents a $C_1$-$C_4$ alkyl group, in particular a methyl group, the deprotection step preferably involves treating porphyrin (4) with a Lewis acid, such as a boron halide, in particular $BBr_3$ or $BCl_3$. The reaction conditions will be suitably chosen by the one skilled in the art, in particular the reaction will be carried out at low temperature, for instance at a temperature between −78° C. and 0° C., for instance between −45° C. and −5° C., in a suitable aprotic solvent, such as toluene or dichloromethane.

The porphyrins of formula (III) according to the present invention wherein at least one of Y, Y, X and X is $CN^+R^7R^8R^9$ or at least one of $R^1$, $R^1$, $R^2$, $R^2$, $R^4$, $R^4$, $R^5$, and $R^5$ is $N^+R^7R^8R^9$, with $R^7$, $R^8$ and $R^9$ as described above, may be prepared following the reaction scheme depicted below.

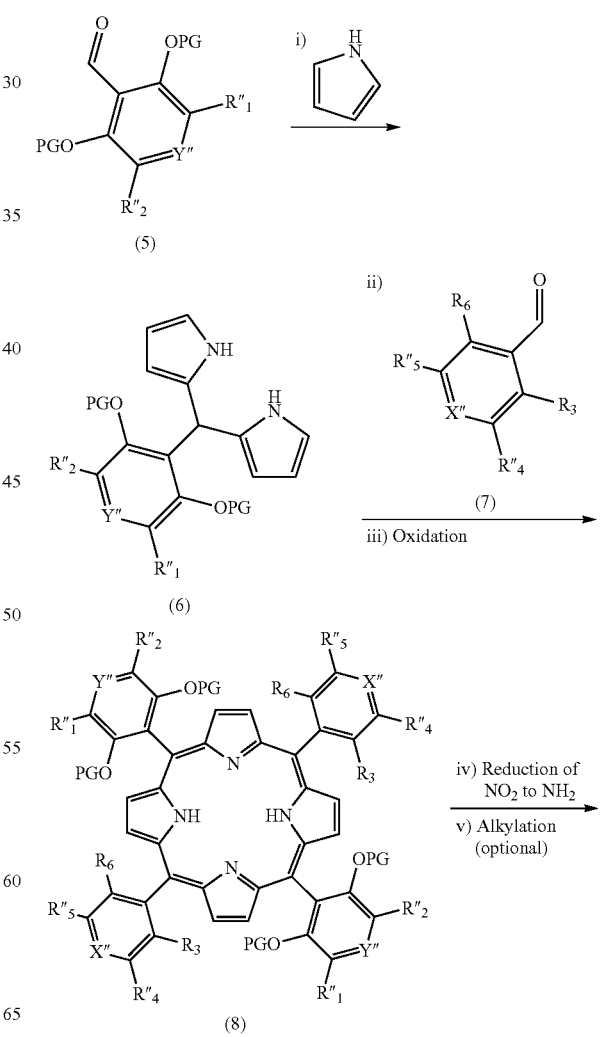

-continued

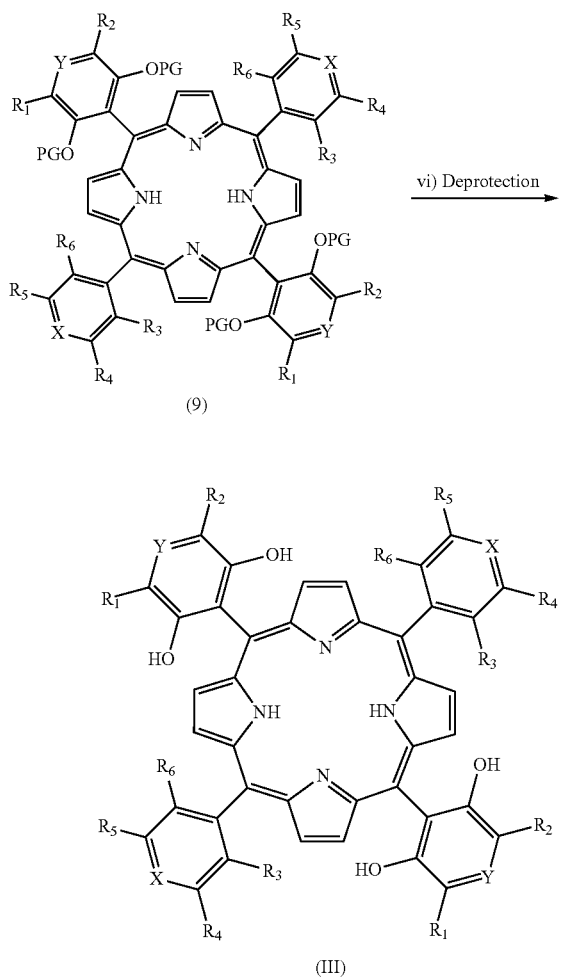

In compounds (5), (6), (7) and (8) above, $R^1$, $R^2$ are independently selected from the group consisting of H, OH, F, $NO_2$, $C_1$-$C_4$ alkyl or $C_1$-$C_4$-alcohol, $R^3$ and $R^6$ are independently selected from the group consisting of H, OH, F and $C_1$-$C_4$-alcohol, $R^4$ and $R^5$ are independently selected from the group consisting of H, OH, F, $C_1$-$C_4$ alkyl, $C_1$-$C_4$-alcohol, or $NO_2$, X independently represent CH, CF, or $CNO_2$, Y independently represent CH, CF, or $CNO_2$, PG stands for Protecting Group. Said PG group is a suitable phenoxy protecting group, preferably selected from the suitable phenoxy protecting groups listed as such in Greene's Protective Groups in Organic Synthesis, Fourth Edition (Peter G. M. Wuts, Theodora W. Greene, John Wiley & Sons, Inc, 2007, ISBN 9780471697541). For instance, PG is a $C_1$-$C_4$ alkyl group, preferably a methyl group, and $R^3$ and $R^6$ are as described above.

The $NO_2$ (nitro) group is used as a precursor for the anilinium group ($N^+R^7R^8R^9$ group).

In step i), substituted aryl aldehyde (5) is condensed with pyrrole leading to dipyrromethane (6). In this first step, at least two equivalents of pyrrole are used. Preferably, pyrrole, advantageously freshly distilled, is used as the solvent. Advantageously, the condensation is carried out under acidic conditions. Therefore, preferably, a carboxylic acid is used in sub-stoichiometric or catalytic amounts, i.e. in 1 to 20 mol %, for instance in 2 to 10 mol %.

Dipyrromethane (6) is then condensed with aldehyde (7), thus providing a tetracyclic intermediate, which is then oxidized to yield porphyrin (8). In other words, dipyrromethane (6) is then condensed with aldehyde (7), and thus subjected to oxidative conditions, thus yielding porphyrin (8). The oxidation substep is preferably carried out using 2,3-dichloro-5,6-dicyanobenzoquinone (DDQ).

Porphyrin (8) is then subjected to reductive conditions, followed by optional alkylation of the resulting amino groups, thus yielding porphyrin (9). The reduction is preferably carried out using tin(II) chloride, advantageously in concentrated hydrochloric acid or ethanol. The optional alkylation step is preferably carried out using methyl iodide, thus yielding the quaternized porphyrin (9). Preferably, the reaction is carried out in the presence of a base, for instance sodium hydride or N,N-diisopropylethylamine.

The following deprotection step is carried out in any suitable manner according to the nature of the PG protecting group of porphyrin (9) and yields porphyrin (III). For instance, when PG represents a $C_1$-$C_4$ alkyl group, in particular a methyl group, the deprotection step preferably involves treating porphyrin (9) with a Lewis acid, such as a boron halide, in particular $BBr_3$ or $BCl_3$. The reaction conditions will be suitably chosen by the one skilled in the art, in particular the reaction will be carried out at low temperature, for instance at a temperature between −78° C. and 0° C., for instance between −45° C. and −5° C., in a suitable aprotic solvent, such as toluene or dichloromethane.

Regarding the synthesis of porphyrins of formula (I), notably wherein X is CH or CF, Y is CH or CF, and $R^4$, $R^4$, $R^5$, and $R^5$ are independently H, OH, F, $C_1$-$C_4$ alkyl or $C_1$-$C_4$ alcohol, the general reaction scheme is very similar, as depicted below.

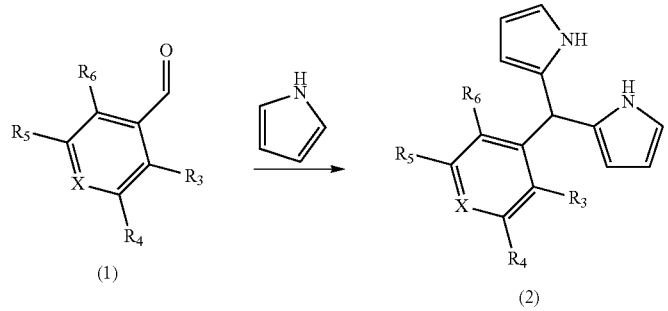

-continued
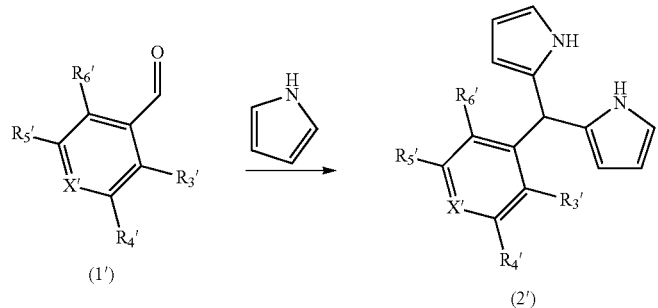
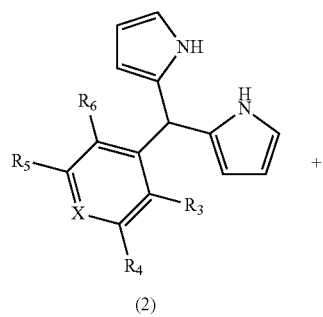
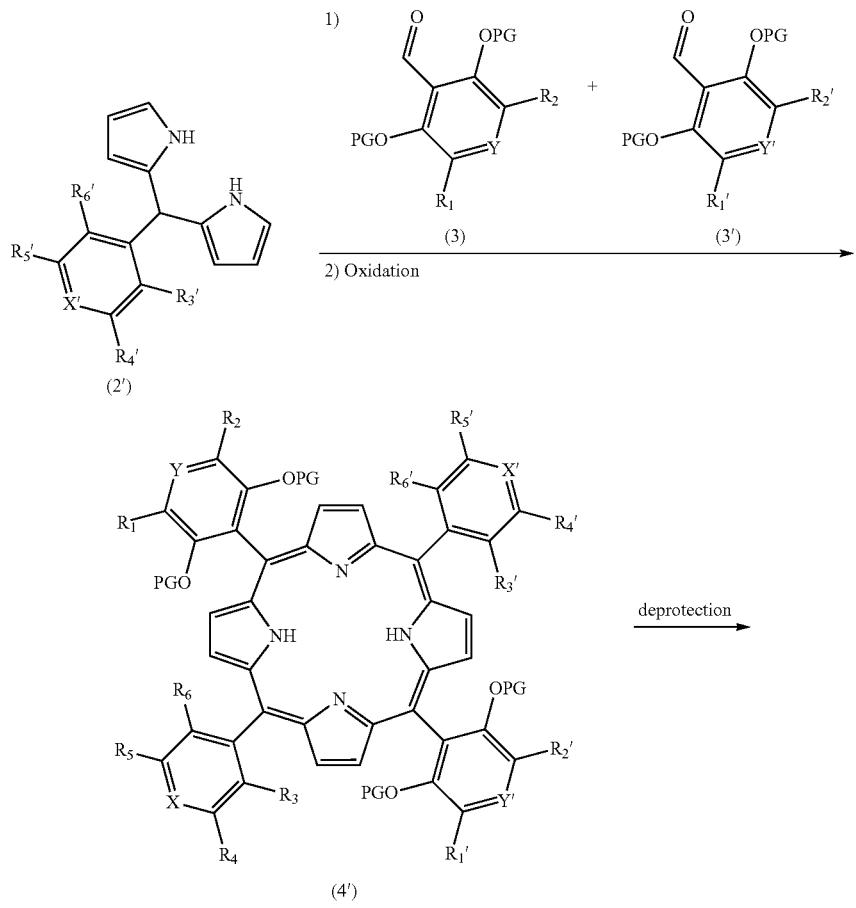

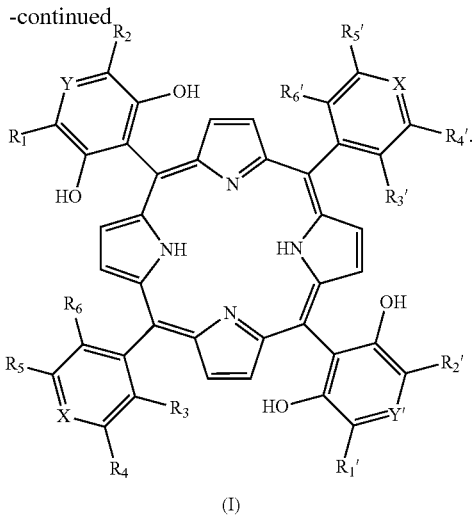

(I)

Similarly, the synthesis of porphyrins of formula (I), notably wherein at least one of Y, Y, X and X is $CN^+R^7R^8R^9$ or at least one of $R^1$, $R^1$, $R^2$, $R^2$, $R^4$, $R^4$, $R^5$, and $R^5$ is $N^+R^7R^8R^9$, with $R^7$, $R^8$ and $R^9$ as described above, may be adapted from the reaction scheme of the corresponding porphyrins of formula (III) represented above.

The following examples, while indicating embodiments of the invention, are intended for purposes of illustration only and are not intended to limit the scope of the invention.

EXAMPLES

Example 1

Synthesis of Perfluorinated Iron Porphyrin FCAT

Synthesis of 5-(Pentafluorophenyl)dipyrromethane

A solution of pentaflurobenzaldehyde (1 mL, 8.1 mmol) in freshly distilled pyrrole (25 mL, 0.375 mol) was degassed by argon for 20 minutes, and then trifluoroacetic acid (60 μL, 0.81 mmol) was added. The mixture was stirred for 30 min at room temperature, then diluted with $CH_2Cl_2$ (200 mL) and washed with 0.1 M NaOH (200 mL). The organic layer was separated, washed with water and dried over $Na_2SO_4$, filtered and the solvent was evaporated at reduced pressure to give brown solid. The residue was purified by column chromatography (silica gel, hexanes/ethyl acetate/triethylamine, 80:20:1). The residue was purified by crystallization (water/ethanol) to yield 5-(Pentafluorophenyl)dipyrromethane as a white powder (1.15 g, 65%). $^1$H NMR (400 MHz, CDCl$_3$): d 5.90 (s, 1H, CH), 6.00-6.05 (m, 2H, ArH), 6.14-6.19 (m, 2H, ArH), 6.71-6.75 (m, 2H, ArH), 8.06 (s, 2H, NH).

5,15-bis(2',6'-dimethoxyphenyl)-10,20-bis(pentafluorophenyl)-21H,23H-porphyrin (1)

To a solution of 5-(pentafluorophenyl)dipyrromethane (1 g, 3.20 mmol) and 2,6-dimethoxybenzaldehyde (532 mg, 3.20 mmol) in dry chloroform (320 mL), previously degassed by argon for 20 minutes, was added $BF_3.OEt_2$ (149 μL, 1.21 mmol) by seringe. The solution was stirred at room temperature under inert atmosphere in the dark for 24 hours, and 2,3-dichloro-5,6-dicyano-1,4-benzoquinone (DDQ) (543 mg, 2.40 mmol) was added to the solution. The mixture was stirred for an additional 24 hours at room temperature, the solution was treated with a second portion of DDQ and refluxed for 2.5 h. The solvent was removed, and the resulting black solid was purified by column chromatography on silica gel using dichloromethane as eluent affording porphyrin 1 (445 mg, 30%) as a purple powder. $^1$H NMR (400 MHz, CDCl$_3$): d−2.69 (s, 2H, NH), 3.53 (s, 12H, OCH$_3$), 7.02 (d, 4H, J=8 Hz ArH), 7.77 (m, 4H, ArH), 8.70 (d, 4H, J=4.8 Hz, H$_{-pyrolic}$) 8.85 (d, 4H, J=4.8 Hz, H$_{-pyrolic}$). HRESI-MS ([M+H]$^+$) calcd for $C_{48}H_{29}F_{10}N_4O_4$ 915.1994. found 915.2024.

5,15-bis(2',6'-dihydroxyphenyl)-10,20-bis(pentafluorophenyl)-21H,23H-porphyrin (2)

To a solution of porphyrin 1 (300 mg, 3.28×10$^4$ mol) in dry dichloromethane (20 mL) at −20° C. was added BBr$_3$ (315 μL, 3.28 mmol). The resulting green solution was stirred for 12 hours at room temperature, and then placed in ice water, ethyl acetate was added to the suspension and the mixture was washed with NaHCO$_3$ until the solution became purple. The organic layer was separated, washed twice with water, filtered and dried over anhydrous Na$_2$SO$_4$. The resulting solution was evaporated. The residue was purified by column chromatography (silica gel, dichloromethane) to yield porphyrin 2 as a purple powder (227 mg, 81%). $^1$H NMR (400 MHz, CDCl$_3$): d−2.80 (s, 2H, NH), 6.97 (d, 4H, J=8 Hz, ArH), 7.63 (t, 2H, J=8 Hz, ArH), 8.87 (d, 4H, J=4.4 Hz, H$_{-pyrolic}$), 9.08 (d, 4H, J=4.8 Hz, H$_{-pyrolic}$). HRESI-MS ([M+H]$^+$) calcd for $C_{44}H_{21}F_{10}N_4O_4$ 859.1388. found 859.1398.

Chloro iron (III) 5,15-bis(2',6'-dihydroxyphenyl)-10,20-bis(pentafluorophenyl)-porphyrin (3)

A solution of compound 2 (100 mg, 1.16×10$^{-4}$ mol), anhydrous iron (II) bromide (452 mg, 2.09 mmol) and 2,6-lutidine (34 μL, 2.9×10$^{-4}$ mol) was heated at 50° C. and stirred 3 hours under inert atmosphere in dry methanol. After methanol was removed, the resulting solid was dissolved in ethyl acetate, washed with 1.2 M HCl solution and then washed until pH was neutral. The crude product was purified by column chromatography (silica gel, 90:10, dichloromethane/methanol) to give compound 3 as a brown solid (108 mg, 98%). HRESI-MS ([M]$^+$) calcd for $C_{44}H_{18}F_{10}N_4O_4$ 912.0512. found 912.0513.

Example 2

Mechanistic Studies for Determining the TOF-Overpotential Relationship Using Cyclic Voltammetry Cyclic voltammetric responses of FCAT and CAT have been studied using the following experimental protocol.

Experimental Section

Chemicals. Dimethylformamide (Acros, >99.8%, extra dry over molecular sieves), the supporting electrolyte NBu$_4$PF$_6$ (Fluka, purriss.), meso-tetraphenylporphyrin iron (III) chloride (Aldrich), phenol (Alfa-Aesar), PhOD (Sigma-Aldrich), were used as received.

Cyclic Voltammetry. The working electrode was a 3 mm-diameter glassy carbon (Tokai) disk carefully polished and ultrasonically rinsed in absolute ethanol before use. The counter-electrode was a platinum wire and the reference electrode an aqueous SCE electrode. All experiments were carried out under argon or carbon dioxide (or a mixing of both gas) at 21° C., the double-wall jacketed cell being thermostated by circulation of water. Cyclic voltammograms were obtained by use of a Metrohm AUTOLAB instrument. Ohmic drop was compensated using the positive feedback compensation implemented in the instrument.

Result

Figure 2:
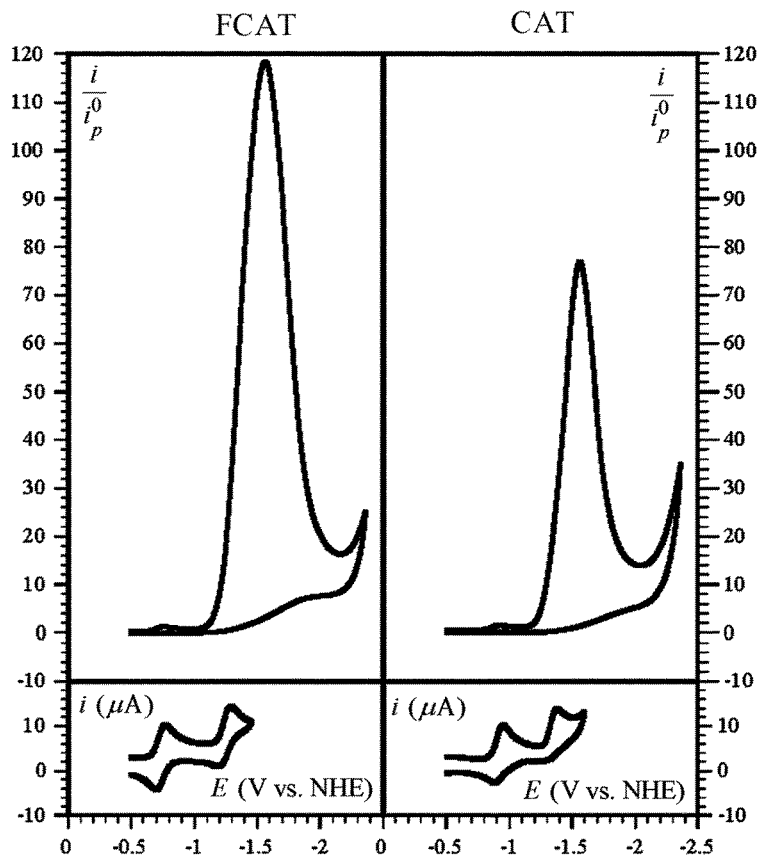
FIG. 2 represents the cyclic voltammetry curves of 1 mM FCAT (bottom left) and CAT (bottom right) in neat DMF+0.1 M n-$Bu_4NPF_6$ at 0.1 $Vs^{-1}$, and the same, top left and top right, respectively, in the presence of 0.23 M $CO_2$ and of 1 M PhOH. The abscissa axis represents E (V vs NHE, in volts), and the ordinate axis represents the current density i (in μA). The peak current of the reversible $Fe^{II}/Fe^I$ wave is a measure of a one-electron transfer.

The results of the cyclic voltammetry studies are presented in FIG. 2.

Figure 3:
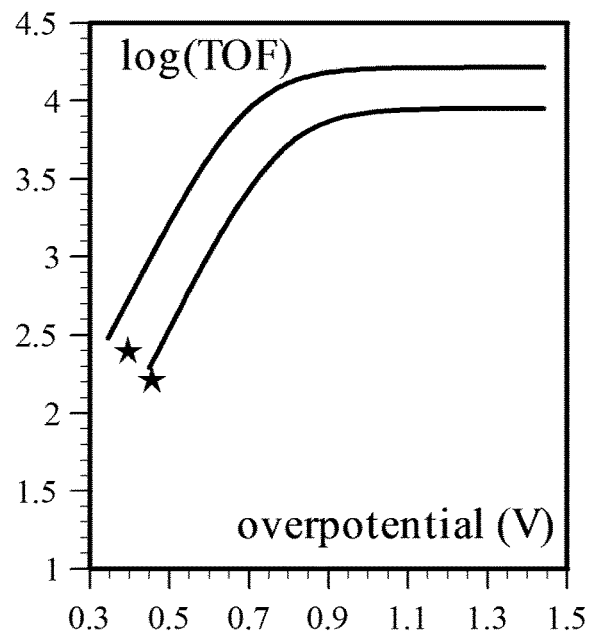
FIG. 3 represents a TOF vs. Overpotential η diagram. The abscissa axis represents the overpotential η (in Volts), and the ordinate axis represents log(TOF). Top curve: FCAT. Bottom curve: CAT. Said curves have been obtained from the kinetic constants determined by Cyclic Voltammetry. The stars represent the electrolysis.
Figure 4:
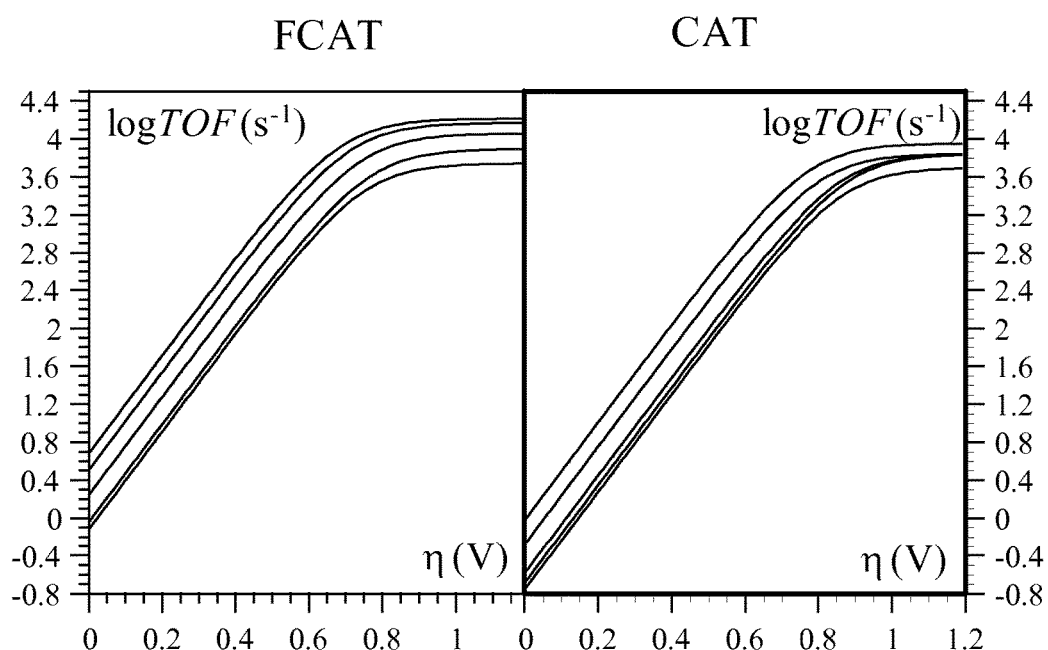
FIG. 4 represents the catalytic Tafel plots derived from cyclic voltammetry experiments for the two catalysts (left: FCAT; right CAT) as a function of the concentration of phenol in the solution, in M: from bottom to top: 0.3, 0.5, 1, 2, 3. The abscissa axis represents the overpotential η (in Volts), and the ordinate axis represents log(TOF). See example 3 for experimental details.

The peak potential is slightly more positive for FCAT (−1.55 V vs. NHE) than for CAT (−1.60 V vs. NHE), while the apparent number of electrons at the peak, at 0.1 V/s is clearly larger in the first case (120) than in the second (80). However a deeper analysis of the meaning of these figures in terms of effective catalysis is required. Comparative cyclic voltammetry of FCAT and CAT catalysts (see FIG. 2) as a function of the scan rate and of the concentrations of CO$_2$ and added phenol has made it possible to unravel the reaction mechanism in spite of the adverse side-phenomena. These cyclic voltammetry studies have also allowed obtaining the Tafel plots presented in FIGS. 3 and 4.

Proposed Mechanism

The presence of prepositioned phenol groups inside the catalyst molecule results in a strong stabilization of the initial Fe(0)CO$_2$ adduct through H-bonding. This positive factor is partly counterbalanced by the necessity, resulting from the same stabilization, to inject an additional electron to trigger catalysis. Thanks to the pre-protonation of the initial Fe(0)CO$_2$ adduct, the potential required for this second electron transfer is not very distant from the potential at which the adduct is generated by addition of CO$_2$ to the Fe(0) complex. The protonation step involves an internal phenolic group and the reprotonation of the phenoxide ion thus generated by added phenol. The prepositioned phenol groups thus play both the role of H-bonding stabilizers and high-concentration proton donors. The second electron transfer step required to close the catalytic loop is a reaction in which electron transfer is concerted with the breaking of one of the two C—O bonds of CO$_2$ and with proton transfer.

Example 3

Electrolysis Results

Cyclic Voltammetry

The working electrode was a 3 mm-diameter glassy carbon (Tokai) disk carefully polished and ultrasonically rinsed in absolute ethanol before use. The counter-electrode was a platinum wire and the reference electrode an aqueous SCE electrode. All experiments were carried out under argon or carbon dioxide at 21° C., the double-wall jacketed cell being thermostated by circulation of water. Cyclic voltammograms were obtained by use of a Metrohm AUTOLAB instrument. Ohmic drop was compensated using the positive feedback compensation implemented in the instrument.

Preparative-scale Electrolysis

Electrolyses were performed using a Princeton Applied Research (PARSTAT 2273) potentiostat. The experiments were carried out in a cell with a carbon crucible as working electrode (S=20 cm$^2$), the volume of the solution is 10 mL. The reference electrode was an aqueous SCE electrode and the counter electrode a platinum grid in a bridge separated from the cathodic compartment by a glass frit, containing a 0.4M Et$_3$NCO$_2$CH$_3$+0.1M NBu$_4$PF$_6$ DMF solution. The electrolysis solution was purged with CO$_2$ during 20 min prior to electrolysis for quantitative experiments and under a continuous flux for the long time scale electrolysis (to avoid the CO$_2$ consumption). The cell configuration is described in *Science* 2012, 338, 90.

The catalyst, FCAT or CAT, is dissolved in the electrolyte solution and is in a concentration of 1 mM.

Fixed-potential electrolyses were performed at −1.08 and −1.14 V vs. NHE with FCAT and CAT, respectively, using a carbon crucible as working electrode under 1 atm CO$_2$ (0.23 M) in the presence of phenol or water as the proton donor. Phenol was used in various concentrations varying from 0.3 to 3 M, while water was used in a concentration of 0.1 M and 3M.

Ohmic drop was minimized as follows: the reference electrode was directly immerged in the solution (without separated bridge) and put progressively closer to the working electrode until oscillations appear. It is then slightly moved away until the remaining oscillations are compatible with recording of the catalytic current-potential curve. The appearance of oscillations in this cell configuration does not require positive feedback compensation as it does with micro-electrodes. The potentiostat is equivalent to a self-inductance. Oscillations thus appear as soon as the resistance that is not compensated by the potentiostat comes close to zero as the reference electrode comes closer and closer to the working electrode surface.

Gaz Detection

Gas chromatography analyses of gas evolved in the course of electrolysis were performed with a HP 6890 series equipped with a thermal conductivity detector (TCD). CO and H$_2$ production was quantitatively detected using a carboPlot P7 capillary column 25 m length and 25 μm in diameter. Temperature was held at 150° C. for the detector and 30° C. for the oven. The carrier gas was argon flowing at constant pressure of 0.5 bars. Injection was performed via a syringe (500 μL) previously degazed with CO$_2$. The retention time of CO was 1.44 min. Calibration curves for H$_2$ and CO were determined separately by injecting known quantities of pure gas.

Results
Selectivity

With both FCAT and CAT catalysts, the faradic yield obtained by analyzing the gas formed after 4 h electrolysis is of 100% in CO, when phenol is used as the proton donor. This result has been observed for experiments wherein phenol was used in a concentration range of between 0.3 M and 3 M.

With FCAT at −1.11V vs NHE, the faradic yield obtained by analyzing the gas formed after 4 h electrolysis is of 87.8% in CO and of 0.5% in H2, when water is used as the proton donor in a concentration of. 0.1 M. When water is used as the proton donor in a concentration of 1.5 M and the electrolysis is carried out at −1.06 vs NHE, the faradic yield obtained by analyzing the gas formed after 4 h electrolysis is of 87.8% in CO and of 11% in $H_2$.

Efficiency in the Presence of Phenol as the Proton Donor

Figure 5:
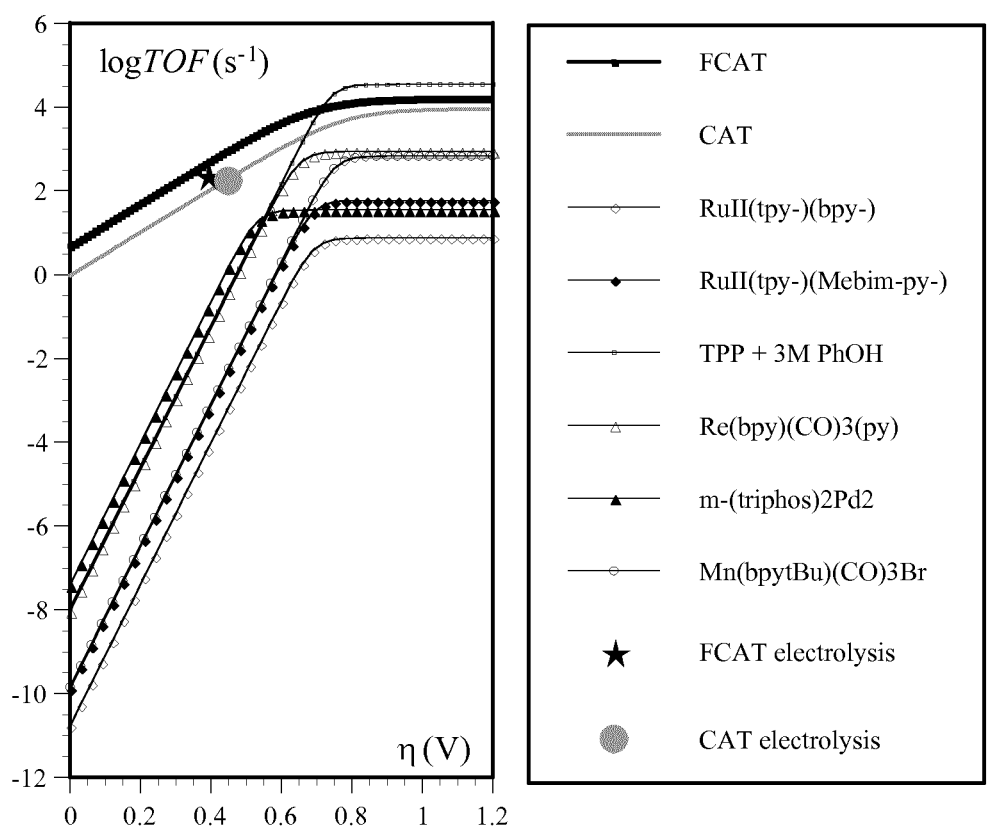
FIG. 5 depicts the benchmarking of all catalysts based on catalytic Tafel plots derived from cyclic voltametry experiments. The abscissa axis represents the overpotential η (in Volts), and the ordinate axis represents log(TOF). FCAT is represented by the star, and CAT by the point. See Table 2 and example 4 for experimental details.

The log TOF-$\eta$ plots (FIG. 4) move upward as the phenol concentration increases. They are more favorable for FCAT than for CAT whatever the concentration of phenol is between 0.1 and 3 M in the electrolyte solution. A more direct comparison between the two catalysts at [PhOH]=3 M is shown in FIG. 5, where the results of preparative-scale electrolyses are also displayed within the same log TOF vs. $\eta$ framework, pointing to the superiority of FCAT over CAT. This is confirmed by preparative-scale electrolyses. Fixed-potential electrolyses were performed at −1.08 and −1.14 V vs. NHE with and FCAT and CAT, respectively, using a carbon crucible as working electrode under 1 atm. $CO_2$ (0.23 M) in the presence of 3 M PhOH. The current $i_{el}/S_{el}$ is stable over 3 h with FCAT and 0.5 h with CAT and the production of CO is practically quantitative (faradic yields of 100±10% and 100±5% respectively, less than 1% $H_2$ is both cases). $i_{el}/S_{el}$=0.5 and 0.3 mA/cm² with FCAT and CAT respectively ($S_{el}$, the working electrode surface area of the preparative-scale electrode electrolysis is much larger, 20 cm², than in CV experiments, 0.07 cm². The corresponding TOF value at the operated overpotential is calculated from TOF= $(i_{el}/i_{pl})$TOF$_{max}$, in which $i_{pl}$ is the plateau current given by equation (1):

$$\frac{i_{pl}}{S} = 2F\sqrt{D_{cat}} \sqrt{k_1[CO_2]} \, C_{cat}^0 \frac{1}{1 + \frac{\sqrt{k_1 C_A^0}}{\sqrt{k_2^{ap}}\left(1 + \frac{\sqrt{k_2^{ap}}}{\sqrt{k_1[CO_2]}}\right)}} \quad (1)$$

$k_1$ is the rate constant corresponding to the addition step of $CO_2$ on Fe(0) (see FIG. 1). $k_2^{ap}$ is a combination of the rate constants of the both steps (2) described in FIG. 1. Both $k_1$ and $k_2^{ap}$ are obtained from the variation of the plateau current in cyclic voltammetry with substrate ($CO_2$) and co-substrate (acid) concentrations and from a pre-wave position at the foot-of-the catalytic wave in cyclic voltammetry.

TOF$_{max}$ is given by:

$$TOF_{max} = 1 \Big/ \left(\frac{1}{k_1 C_A^0} + \frac{1}{k_2^{ap}}\right)$$

The TOF values thus obtained are 240 s⁻¹ (at $\eta$=0.39 V) and 168 s⁻¹ (at $\eta$=0.45 V) for FCAT and CAT, respectively.

These results are summarized in table 1 below.

TABLE 1

| catalyst | $\eta$ (V) | TOF$_{max}$ (s⁻¹) | $i_{pl}$ (mA) | S (cm²) | I (mA/cm²) | TOF (s⁻¹) | log TOF |
|---|---|---|---|---|---|---|---|
| CAT + 3M PhOH | 0.45 | 8962 | 1.681 | 0.07 | 0.3 | 168 | 2.225 |
| FCAT + 3M PhOH | 0.39 | 16351 | 2.17 | 0.07 | 0.5 | 240 | 2.42 |

Durability (Stability of the Catalysts)

Besides catalytic performances evaluated through log TOF-$\eta$ relationship, durability is important in the evaluation of catalysts efficiency. It has been evaluated through estimation of the catalyst degradation over prolonged electrolysis. This estimation is based on recording CVs in the electrolysis solution during electrolysis. It turns out that, FCAT is more stable than CAT or simple FeTPP. Complete degradation of the initial 10⁻⁵ moles of catalyst is observed after the passage of 575, 200 and 290 Coulombs for FCAT, CAT and simple FeTPP, corresponding to 600, 210 and 300 catalytic cycles for FCAT, CAT and FeTPP, respectively.

Therefore, catalyst CAT is totally degraded after 14 h of electrolysis. This result allows to infer that the TON of CAT is of $$210 \left(TON = \frac{Q/F}{n_{cat}^0} = 210\right).$$

Regarding FCAT, degradation is slower. Complete degradation is observed after 35 h of electrolysis and use of 575 C, that is to say FCAT has a TON of 600.

Example 4

Benchmarking of FCAT with Prior Art Complexes

TABLE 2

Comparison of FCAT and CAT with other catalysts of the $CO_2$/CO conversion.[a]

| Ref | Solvent + acid $E_{CO_2/CO}^0$ | Catalyst $E_{cat}^0$ | $k_1^{ap}CO_2$ $k_2^{ap}$ | logTOF$_{max}$ (s⁻¹) | logTOF$_0^c$ (s⁻¹)[c] |
|---|---|---|---|---|---|
| 1 | DMF +3M PhOH −0.69 | Fe⁰TPP −1.43 | 3.5 × 10⁴[b] | 4.5 | −8 |
| 2 | DMF +0.1M HBF₄ −0.23 | m-(triphos)₂Pd₂[d] −0.76 | 35[b] | 1.5 | −07.4 |
| 3 | $CH_3CN$ +0.8M $CF_3CH_2OH$ −0.65 | Re(bpy)(CO)₃(py)[e] −1.30 | 875[b] | 2.9 | −8 |
| 4 | $CH_3CN$ +1.4M $CF_3CH_2OH$ −0.65 | Mn(bpytBu)(CO)₃Br[e] −1.40 | 680[b] | 2.8 | −9.8 |

TABLE 2-continued

| | | | | | |
|---|---|---|---|---|---|
| Comparison of FCAT and CAT with other catalysts of the $CO_2/CO$ conversion.[a] | | | | | |
| Ref | Solvent + acid $E_{CO_2/CO}^0$ | Catalyst $E_{cat}^0$ | $k_1^{ap}[CO_2\overset{\cdot}{B}]$ $k_2^{ap}$ | $logTOF_{max}$ $(s^{-1})$ | $logTOF_0^c$ $(s^{-1})^c$ |
| 5 | $CH_3CN$ | $Ru^{II}(tpy^-)(bpy^-)^e$ −1.34 | 7.6[b] | 0.9 | −10.8 |
| 5 | $CH_3CN$ | $Ru^{II}(tpy^-)(Mebim\text{-}py^-)^e$ −1.34 | 59[b] | 1.8 | −9.9 |

[a]potentials in V vs. NHE, first order or pseudo first order rate constants in $s^{-1}$.
[b]$k_2^{ap} \gg k_1^{ap}[CO_2\overset{\cdot}{B}]$.
[c]TOF at $\eta = 0$.

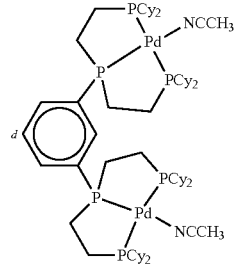

[e]py = pyridine, tpy = 2,2':6',2''-terpyridine, bpy = 2,2'-bipyridine, Mebimpy = 2,6-bis(1-methyl benzimidazol-2-yl)pyridine Table 2 summarizes the various parameters that were extracted from previous reports. FIG. 5 illustrates the ensuing benchmarking of all catalysts. In terms of preparative scale electrolyses, the available pieces of information indicate that the stability of the catalysts are of the same order as for the two catalysts FCAT and CAT described here. Without wishing to be bound by theory, the conclusion is twofold.

(i) The iron porphyrin generated electrochemically under its $Fe^0$ form (FCAT) operated in the presence of 3 M phenol in DMF appears as the best homogeneous catalyst of the $CO_2$-to-CO conversion to date. This clearly appears after benchmarking of presently available catalyst of this reaction under the form of catalytic Tafel plots relating turnover frequency with overpotential (FIG. 5). Such plot allows optimizing the catalytic reaction by appropriately compromising between rapidity and energy costs. A further advantageous feature of FCAT is that it relies on one of the cheapest and most earth-abundant metal.

(ii) Fluorine substitution in passing from CAT to FCAT was expected to favor catalysis in terms of overpotential thanks to the inductive effect of the fluorine substituents. At the same time, it was expected to render the follow-up reactions less favorable possibly annihilating the initial favorable effect of fluorine substitution or even making catalysis globally less efficient than with CAT. However, it was observed that this is not the case, and that the substitution has a global positive effect.

Example 5

Synthesis of Tetra-anilinium Catalyst

The tetra-anilinium iron complex according to the present invention is synthesized according to the following reaction scheme.

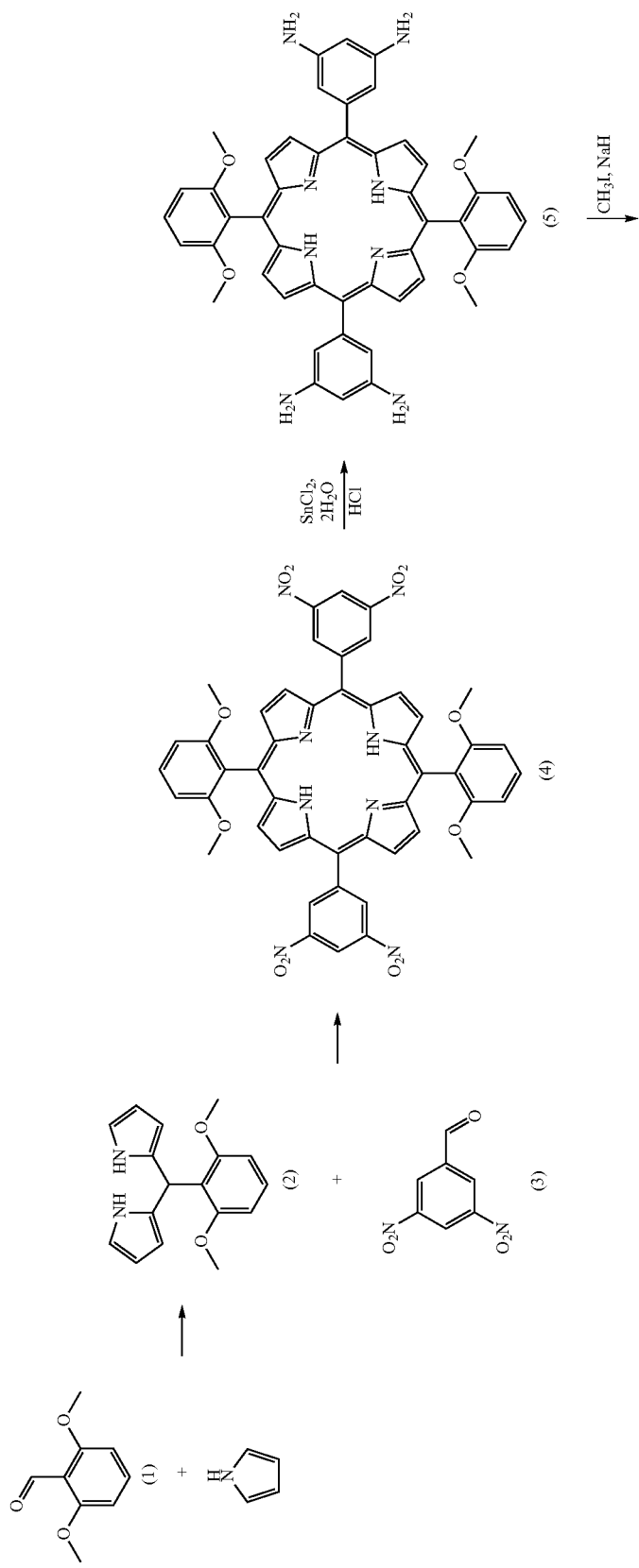

-continued
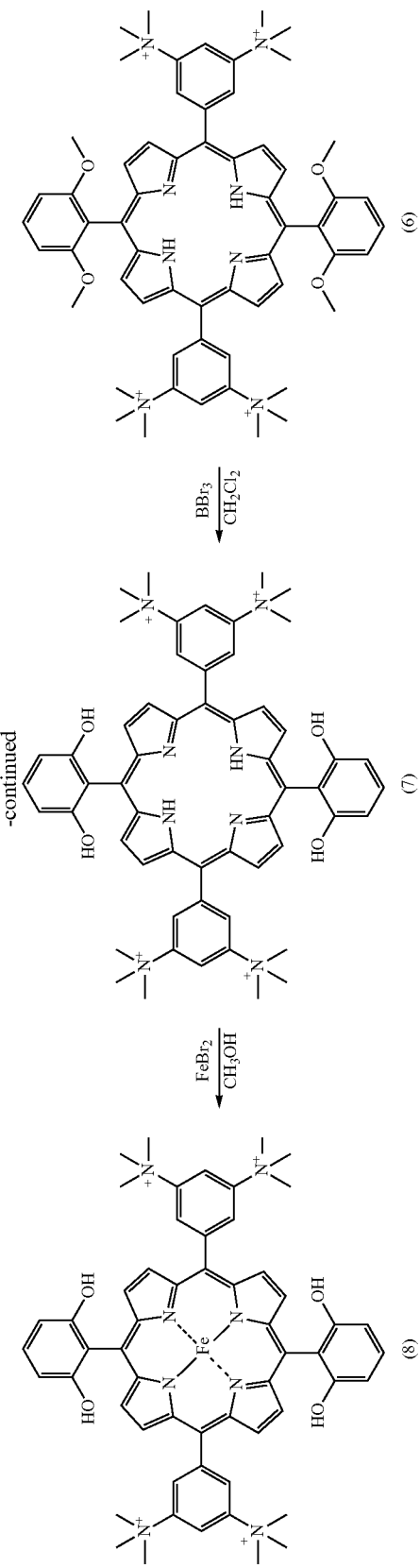

Example 6

Synthesis of FeDHPTMA for Catalysing the Electrochemical Reduction of CO2 into CO in Water or in DMF and Cyclic Voltammetry Experiments Chemicals. Methanol and Dichloromethane were distilled over calcium hydride; Chloroform was distilled over calcium chloride; THF was dried over sodium then distilled after addition of benzophenone. Both solvents were freshly distilled or stored overnight under an argon atmosphere. All other starting materials were obtained from Sigma-Aldrich, Fluka, Alfa Aesar, and Merk; they were used as received without further purification. 1H NMR spectra were recorded on a Bruker Avance III 400-MHz spectrometer and were referenced to the resonances of the solvent used.

Synthetic scheme.

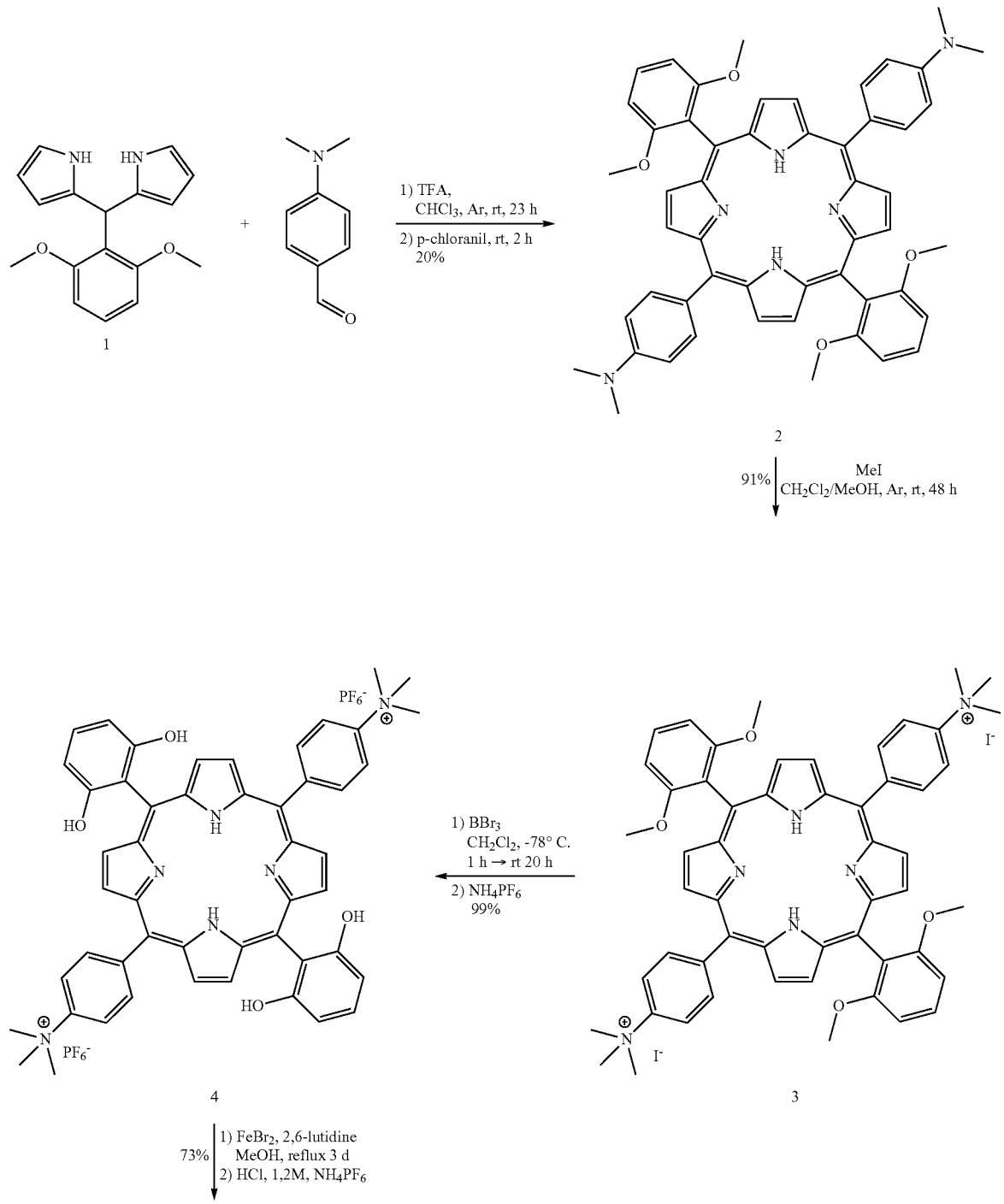

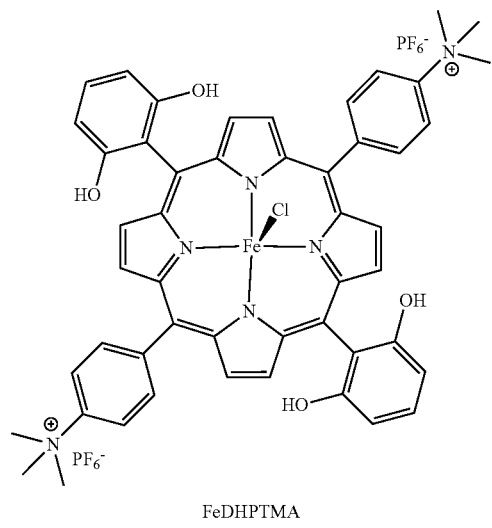

FeDHPTMA

Synthesis.

2. Dipyrromethane 1 (100 mg, $3.5 \times 10^{-4}$ mol) and 4-(Dimethylamino)benzaldehyde (52.8 mg, $3.5 \times 10^{-4}$ mol) were solubilized in chloroform (56 mL). After the solution has been degassed with argon for 30 minutes, trifluoroacetic acid (27.1 µL, $3.5 \times 10^{-4}$ mol) was added dropwise and the mixture was stirred under argon for 23 h in the dark. After that, p-chloranil (261.3 mg, $1.1 \times 10^{-3}$ mol) was added in one portion and the mixture was stirred 2 h. The dark purple mixture was filtered through a short pad of silica ($CH_2Cl_2$/MeOH 100/0 to 95/5 as eluent). After evaporation of the solution, the residue was purified by column chromatography on silica gel (gradient elution from $CHCl_3$/Ethyl Acetate=100/0 to 95:5) to give 2 as a purple powder (56 mg, 20%).

$^1$H NMR (400 MHz, $CD_2Cl_2$) 8.86 (d, J=4.7 Hz, 4H), 8.74 (d, J=4.7 Hz, 4H), 8.06 (d, J=8.6 Hz, 4H), 7.77 (t, J=8.5 Hz, 2H), 7.11 (d, J=8.7 Hz, 4H), 7.06 (d, J=8.5 Hz, 4H), 3.56 (s, 12H), 3.21 (s, 12H), −2.66 (s, 2H).

3. Iodomethane (0.5 mL, $8.04 \times 10^{-3}$ mol) was added to a solution of 2 (15 mg, $1.8 \times 10^{-5}$ mol) in a freshly distilled $CH_2Cl_2$/MeOH (3/0.5 mL) mix. After the mixture has been stirred under argon for 48 h in the dark, it was slowly poured in a large volume of diethyl ether. A solid purple precipitate was isolated by filtration and washed with $CH_2Cl_2$ to give 3 as a purple powder (18 mg, 91%)

$^1$H NMR (400 MHz, $CD_3CN$) 8.85 (d, J=4.6 Hz, 4H), 8.75 (d, J=4.6 Hz, 4H), 8.46 (d, J=9.0 Hz, 4H), 8.16 (d, J=9.0 Hz, 4H), 7.85 (t, J=8.5 Hz, 2H), 7.16 (d, J=8.6 Hz, 4H), 3.84 (s, 18H), 3.53 (s, 12H), −2.83 (s, 2H).

4. BBr3 (0.24 mL, $2.53 \times 10^{-3}$ mol) was added dropwise to a suspension of porphyrin 3 (70 mg, $6.3 \times 10^{-5}$ mol) in freshly distilled $CH_2Cl_2$ (20 mL) at −78° C. and the suspension was stirred at this temperature for 1 h. The green reaction mixture was allowed to warm to room temperature and was stirred overnight. Excess BBr3 was quenched by the slow addition of MeOH (3 mL) at 0° C. The solvent was removed in vaccuo and the green residue was solubilized in water (10 mL) and 3 drops of a $NH_4HCO_3$ saturated aqueous solution were added until the solution turned from green to red. The porphyrin was precipitated by the addition of $NH_4PF_6$ (500 mg), isolated by filtration and was successively washed with a $NH_4PF_6$ aqueous solution (50 mg in 10 mL), water (5 mL), a propan-2-ol/$Et_2O$ 1/1 mix (20 mL) and $CH_2Cl_2$ (20 mL) to yield 4 as a purple powder (68 mg, 99%)

$^1$H NMR (400 MHz, $CD_3CN$) 8.96 (d, J=4.5 Hz, 4H), 8.81 (d, J=4.5 Hz, 4H), 8.47 (d, J=7.7 Hz, 4H), 8.16 (d, J=7.7 Hz, 4H), 7.55 (t, J=8.2 Hz, 2H), 6.87 (d, J=8.2 Hz, 4H), 6.78 (s br, 4H), 3.83 (s, 18H), −2.80 (s, 2H).

FeDHPTMA. A solution of 4 (55 mg, $5.1 \times 10^{-5}$ mol), anhydrous iron (II) bromide (219 mg, $1.0 \times 10^{-3}$ mol), and 2,6-lutidine (15 µL, $1.3 \times 10^{-4}$ mol) in dry methanol (10 mL) was degassed by Argon for 15 minutes; the mixture was stirred at reflux under inert atmosphere for 3 days. After methanol was removed, the resulting solid was solubilized in water (10 mL). To this solution was added 1.2M HCl (10 mL), followed by $NH_4PF_6$ (500 mg). A brown solid was isolated by filtration and washed successively with a NH4PF6 aqueous solution (50 mg in 10 mL), water (5 mL), a propan-2-ol/Et2O 1/1 mix (20 mL) and $CH_2Cl_2$ (20 mL) to give FeDHPTMA as a dark red powder (43.8 mg, 73%)

Cyclic Voltammetry.

Figure 6:
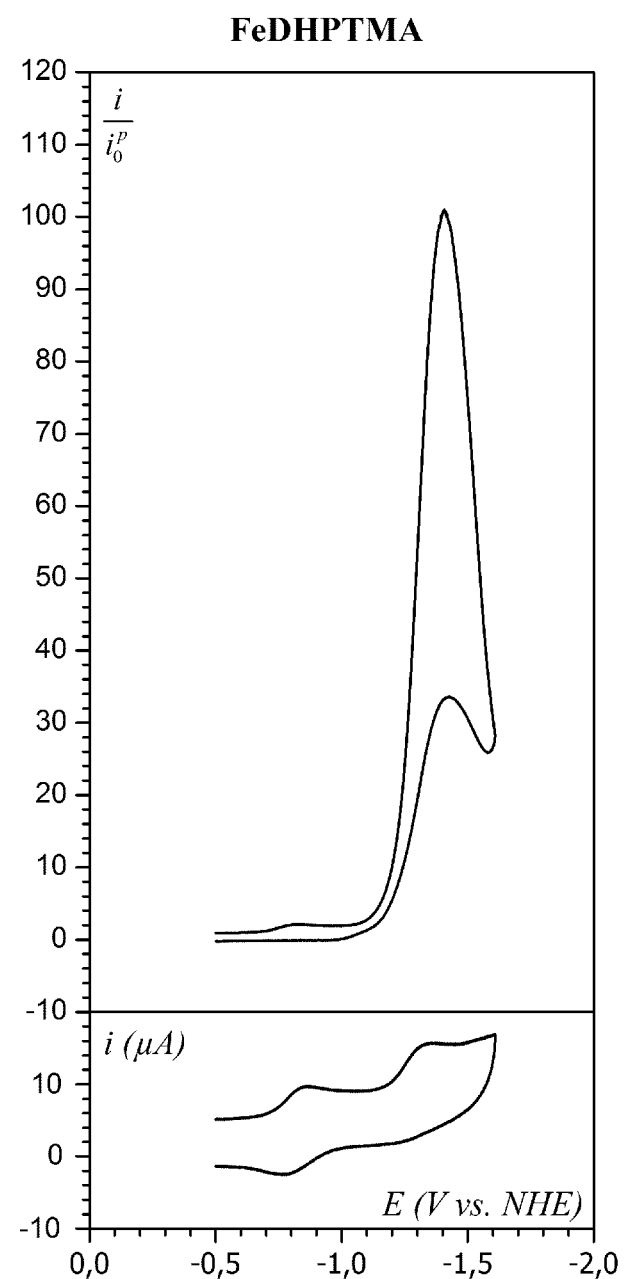
FIG. 6 represents the cyclic voltammetry curves of 0.5 mM FeDHPTMA in neat DMF+0.1 M n $Bu_4NPF_6$ at 0.2 $V.s^{-1}$ (bottom), and the same (top) in the presence of 0.23 M $CO_2$ and of 0.5 M PhOH. The abscissa axis represents E (V vs NHE, in volts), and the ordinate axis represents the current density i (in μA). The peak current of the reversible $Fe^{II}/Fe^I$ wave is a measure of a one-electron transfer.

The results of the cyclic voltammetry studies are presented in FIG. 6.

The peak potential is slightly more positive for FeDHPTMA (−1.41 V vs. NHE) than for CAT (−1.60 V vs. NHE), while the apparent number of electrons at the peak, at 0.2 V/s is clearly larger in the first case (100) than in the second (80).

Example 7

Three other porphyrins can be used for catalysing the electrochemical reduction of $CO_2$ into CO in water or in DMF.

The first porphyrin is:
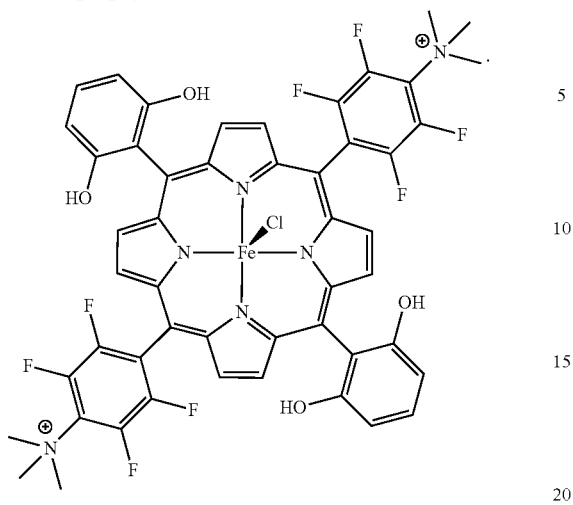
The preparation of material for realizing the second porphyrin is for instance:
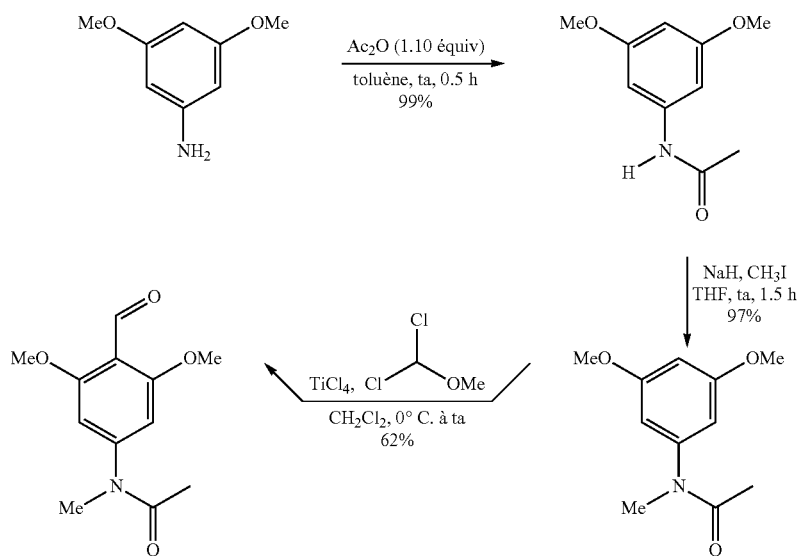
The second porphyrin is:
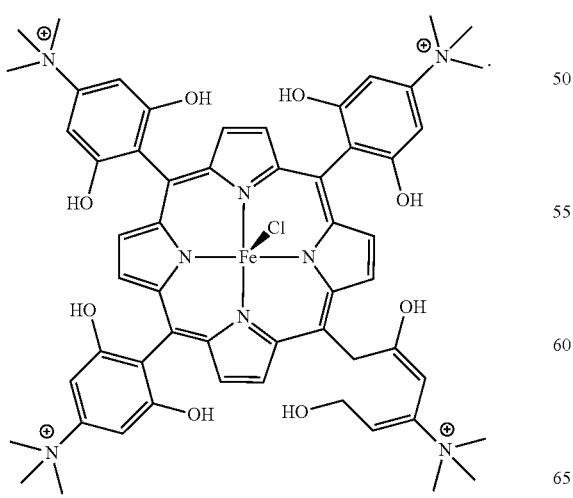
The synthesis of the second porphyrin is for instance:

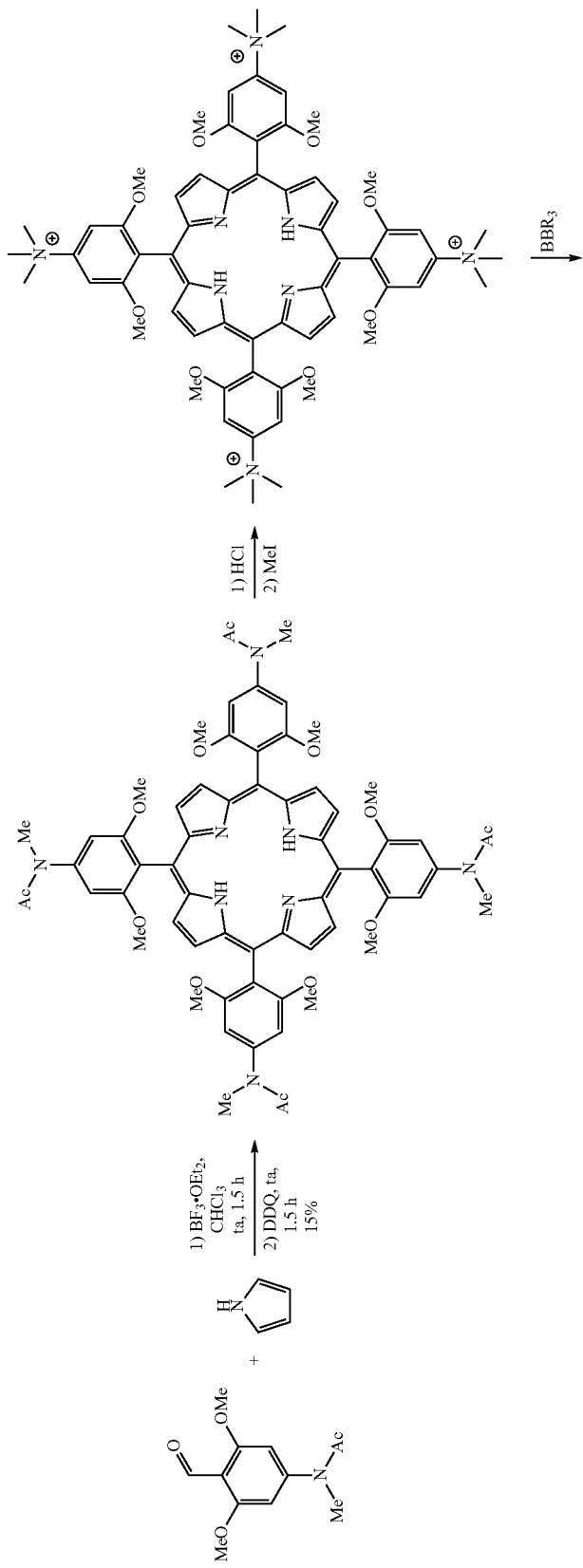

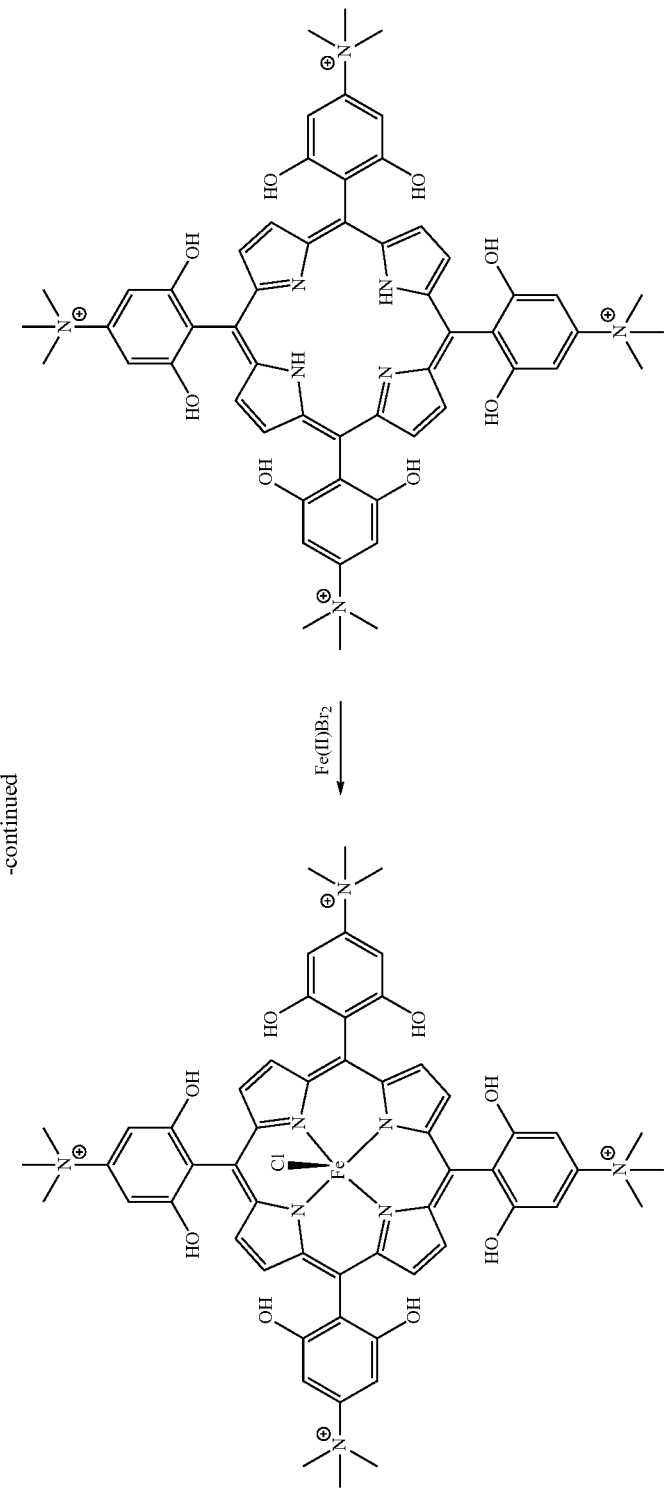

with Ac: «acetyl»—COCH₃

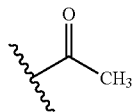

The third porphyrin is:

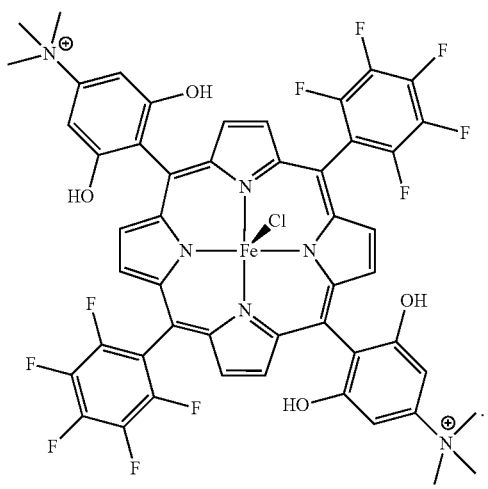

The invention claimed is:
1. A porphyrin of formula (I):

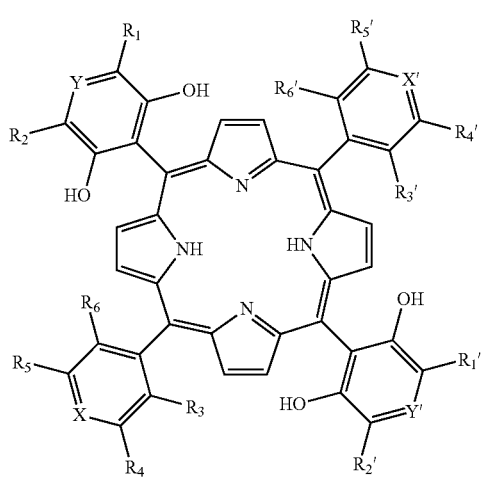

wherein
$R^1$, $R^{1'}$, $R^2$ and $R^{2'}$ independently represent H, OH, F, $N^+R^7R^8R^9$, $C_1$-$C_4$ alkyl or $C_1$-$C_4$-alcohol, $R^3$, $R^{3'}$, $R^6$ and $R^{6'}$ are independently selected from the group consisting of H, OH, F and $C_1$-$C_4$-alcohol, $R^4$, $R^{4'}$, $R^5$, $R^{5'}$ are independently selected from the group consisting of H, OH, F, $C_1$-$C_4$ alkyl, $C_1$-$C_4$-alcohol, or $N^+R^7R^8R^9$, X and X' independently represent CH, CF, $CN^+R^7R^8R^9$, or $N^+R^7$, Y and Y' independently represent CH, CF, $CN^+R^7R^8R^9$, or $N^+R^7$, $R^7$, $R^8$ and $R^9$ independently of each other represent H or a $C_1$-$C_4$ alkyl group, provided that at least one of X, X', Y and Y' represents CF, $CN^+R^7R^8R^9$, or $N^+R^7$, or at least one of $R^3$, $R^{3'}$, $R^6$ and $R^{6'}$ represents F or at least one of $R^1$, $R^{1'}$, $R^2$, $R^{2'}$, $R^4$, $R^{4'}$, $R^5$, and $R^{5'}$ represents F or $N^+R^7R^8R^9$, and salts thereof.

2. The porphyrin of claim 1, wherein at least one of X, X', Y or Y' represents CF, $CN+R^7R^8R^9$, or $N^+R^7$ or at least one of $R^1$, $R^{1'}$, $R^2$, $R^{2'}$, $R^4$, $R^{4'}$, $R^5$, $R^{5'}$ represents F or $N^+R^7R^8R^9$, with $R^7$, $R^8$ and $R^9$ are as described in claim 1.

3. The porphyrin of claim 1, wherein it is of formula (III):

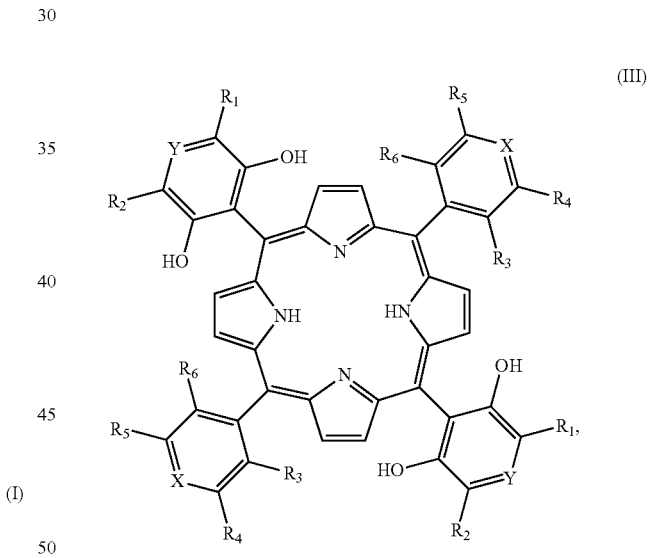

with $R^1$, $R^2$, $R^3$, $R^4$, $R^5$, $R^6$, X and Y are as defined in claim 1.

4. The porphyrin of claim 1, wherein X and X' independently represent CH or CF.

5. The porphyrin of claim 1, wherein $R^3$, $R^{3'}$, $R^4$, $R^{4'}$, $R^5$, $R^{5'}$, $R^6$, and $R^{6'}$ are independently selected from the group consisting of H and F.

6. The porphyrin of claim 1, wherein at least one of Y, Y', X and X' is $CN^+R^7R^8R^9$ or at least one of $R^1$, $R^{1'}$, $R^2$, $R^{2'}$, $R^4$, $R^{4'}$, $R^5$, and $R^{5'}$ is $N^+R^7R^8R^9$, with $R^7$, $R^8$ and $R^9$ defined in claim 1.

7. The porphyrin of claim 6, wherein it is of the following formula:

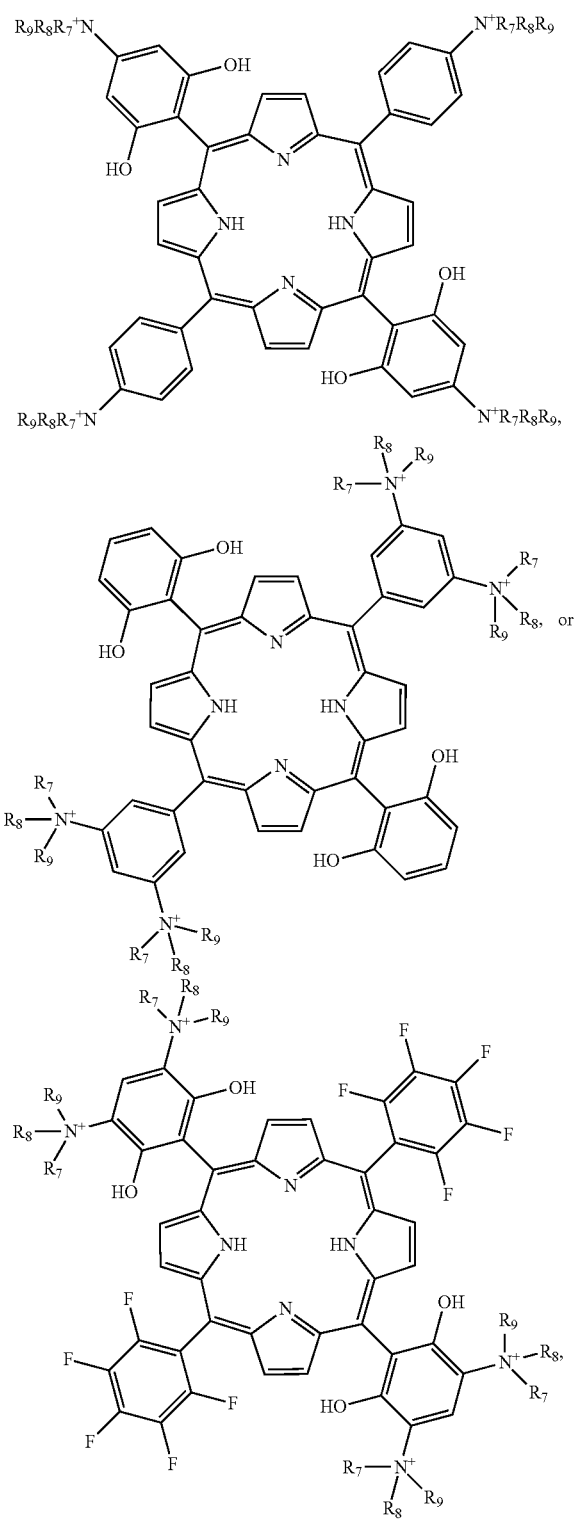

wherein $R^7$, $R^8$ and $R^9$ as independently of each other represent H or a $C_1$-$C_4$ alkyl group.

8. The porphyrin of claim 1, wherein it is:

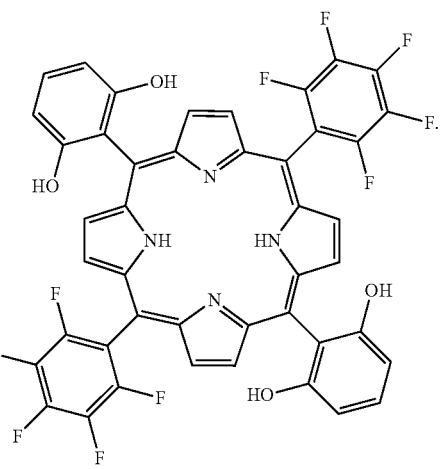

9. A complex of a porphyrin according to claim 1 with a transition metal and salts thereof.

10. The complex of claim 9, wherein the transition metal is iron.

11. An electrochemical cell comprising at least:
   an electrolyte solution comprising the solvent, a supporting electrolyte, and the substrate $CO_2$,
   a power supply providing the energy necessary to trigger the electrochemical reactions involving the substrate, and
   two electrodes, an anode and a cathode,
   wherein the electrochemical cell further comprises the complex of claim 8.

12. The electrochemical cell of claim 11, wherein the complex is in a concentration, in the electrolyte solution, of between 0.0005 and 0.01 M.

13. The electrochemical cell of claim 11, wherein the electrolyte further comprises a proton donor selected from the group consisting of water ($H_2O$), trifluoroethanol, phenol and acetic acid.

14. The electrochemical cell of claim 11, wherein the complex is in the electrolyte solution.

15. A method of reducing electrochemically $CO_2$ into CO using the complex of claim 9 as catalyst or an electrochemical cell comprising at least:
   an electrolyte solution comprising the solvent, a supporting electrolyte, and the substrate $CO_2$,
   a power supply providing the energy necessary to trigger the electrochemical reactions involving the substrate,
   two electrodes, an anode and a cathode, and
   the complex of claim 9.

16. The method of claim 15, wherein the method is carried out in the presence of a proton donor.

17. The method of claim 15, wherein the potential applied to the cathode is between −2.5 V and −0.5 V versus NHE.

18. The method of claim 15, wherein the proton donor is selected from the group consisting of water, trifluoroethanol, phenol and acetic acid.

19. The method of claim 15, wherein the intensity applied to the cathode is between 2 and 5 $A/m^2$.

* * * * *